United States Patent
Khvorova et al.

(10) Patent No.: US 10,844,377 B2
(45) Date of Patent: Nov. 24, 2020

(54) TWO-TAILED SELF-DELIVERING SIRNA

(71) Applicant: UNIVERSITY OF MASSACHUSETTS, Boston, MA (US)

(72) Inventors: Anastasia Khvorova, Westborough, MA (US); Julia Alterman, Worcester, MA (US); Matthew Hassler, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 19 days.

(21) Appl. No.: 16/015,440

(22) Filed: Jun. 22, 2018

(65) Prior Publication Data

US 2019/0024082 A1 Jan. 24, 2019

Related U.S. Application Data

(60) Provisional application No. 62/523,949, filed on Jun. 23, 2017.

(51) Int. Cl.
*C12N 15/113* (2010.01)

(52) U.S. Cl.
CPC ........ *C12N 15/113* (2013.01); *C12N 2310/14* (2013.01); *C12N 2310/314* (2013.01); *C12N 2310/315* (2013.01); *C12N 2310/321* (2013.01); *C12N 2310/322* (2013.01); *C12N 2310/343* (2013.01); *C12N 2310/344* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 5,814,014 | A | 9/1998 | Elsberry |
| 6,093,180 | A | 7/2000 | Elsberry |
| 6,107,094 | A | 8/2000 | Crooke |
| 2003/0143732 | A1 | 7/2003 | Fosnaugh et al. |
| 2008/0188429 | A1* | 8/2008 | Iyer ............ C12N 15/1131 514/44 A |
| 2009/0306178 | A1* | 12/2009 | Bhat ............ A61K 31/7125 514/44 A |
| 2015/0267200 | A1 | 9/2015 | McSwiggen |
| 2015/0315584 | A1 | 11/2015 | MacDonald |
| 2016/0319278 | A1 | 11/2016 | Khvorova |

OTHER PUBLICATIONS

Alvarez-Erviti et al., (2011) "Delivery of siRNA to the mouse brain by systematic injection of targeted exosomes," Nature Biotechnology, 29(4):341-345.
Braasch et al., (2003) "RNA Interference in Mammalian Cells by Chemically-Modified RNA," Biochemistry, 42:7967-7975.
Egusquiaguirre et al., (2012) "Nanoparticle delivery systems for cancer therapy: advances in clinical and preclinical research," Clin. Transl. Oncol., 14:83-93.
El Andaloussi et al., (2013) "Extracellular vesicles: biology and emerging therapeutic opportunities," Nature Reviews, 12:347-357.
El Andaloussi et al., (2013) "Exosomes for targeted siRNA delivery across biological barriers," Advanced Drug Delivery Reviews, 65:391-397.
El Andaloussi et al., (2012) "Exosome-mediated delivery of siRNA in vitro and in vivo," Nature Protocols, 7(12):2112-2126.
Elmen et al., (2005) "Looked nucleic acid (LNA) mediated improvements in siRNA stability and fucntionality," Nucleic Acids Research, 33(1):439-447.
Fattal et al., (1998) "Biodegradable polyalkycyanoacrylate nanoparticles for the delivery of oligonucleotides," Journal of Controlled Release, 53:137-143.
Godard et al., (1995) "Antisense effects of cholesterol-oligodeoxynucleotide conjugates associated with poly (alkylcyanoacrylate) nanoparticles," Eur. J. Biochem., 232:404-410.
Lambert et al., (2001) "Nanoparticles systems for the delivery of antisense oligonucleotides," Advanced Drug Delivery Reviews, 47:99-112.
Lee et al., (2013) "Recent Developments in Nanoparticles-Based siRNA Delivery for Cancer Therapy," BioMed Reseach International, 10 pages.
Nielsen et al., (1991) "Sequence-Selective Recognition of DNA by Strand Displacement with a Thymine-Substituted Polyamide," Science, 1497-1500.
Petersen et al., (2003) "LNA: a versatile tool for therapeutics and genomics," Trends in Biotechnology, 21(2):74-81.
Wang et al., (2010) "Nanoparticle-Based delivery system for application of siRNA in Vivo," Current Drug Metabolism, 11:182-196.
Yuan et al., (2011) "Recent advances of siRNA delivery by nanoparticles," Expert Opin. Drug Deliv., 8(4):521-536.
International Search Report and Written Opinion for International Application No. PCT/US2018/38952, dated Sep. 24, 2018.

* cited by examiner

*Primary Examiner* — Tracy Vivlemore
(74) *Attorney, Agent, or Firm* — Lathrop GPM LLP; James H. Velema, Esq.; Michael J. Spellberg

(57) ABSTRACT

Provided are compositions and methods comprising two-tailed siRNAs (tt-siRNAs) that exhibit unprecedented cellular uptake and silencing. Also provided are methods of treating neurological and other diseases with the two-tailed siRNAs of the invention.

30 Claims, 13 Drawing Sheets

TWO-TAILED SELF-DELIVERING SIRNA

CROSS-REFERENCE TO RELATED APPLICATION

This application claims the benefit of U.S. Provisional Application Ser. No. 62/523,949 filed Jun. 23, 2017, the entire disclosure of which is hereby incorporated herein by reference.

STATEMENT OF FEDERALLY SPONSORED RESEARCH

This invention was made with government support under Grant numbers GM108803 and DO020012 awarded by the National Institutes of Health. The Government has certain rights in the invention.

TECHNICAL FIELD

This disclosure relates to novel two-tailed siRNA compounds useful for RNA interference (RNAi), consisting of chemically-modified ribonucleotides and two overhanging, single-stranded tails. The chemically-modified nucleotides are patterned to achieve unexpectedly high efficacy, uptake and tissue distribution.

BACKGROUND

Therapeutic RNA oligonucleotides (e.g., siRNA) comprising chemically-modified ribonucleotides (e.g., 2'-fluoro and 2'-methoxy modifications) and/or chemically-modified linkers (e.g., a phosphorothioate modification) are known to exhibit increased nuclease resistance relative to the corresponding unmodified oligonucleotides, while maintaining the ability to promote RNAi. See, e.g., Fosnaugh, et al. (U.S. Publication No. 2003/0143732).

There remains a need, however, for robust and non-toxic delivery to specific cell types in vivo, especially for delivery to central nervous system tissues, in order to efficiently deliver RNAi for the treatment of neurological and other diseases.

SUMMARY

The present invention is based on the discovery of novel two-tailed, chemically-modified oligonucleotides that can function as new class of siRNA therapeutics. Surprisingly, it was discovered that two-tailed, chemically-modified siRNAs (tt-siRNAs) demonstrated widespread distribution and retention after both intrastriatal and intracerebroventricular injection, above that which was observed for single-tailed siRNA.

Accordingly, in one aspect of the invention, provided herein is a double-stranded nucleic acid compound comprising: a sense strand having a 5' end, a 3' end and a region of complementarity with an antisense strand; an antisense strand having a 5' end, a 3' end and a region of complementarity with the sense strand and a region of complementarity to an mRNA target; an overhang region at the 3' end of the sense strand having at least 3 contiguous phosphorothioated nucleotides; and an overhang region at the 3' end of the antisense strand having at least 3 contiguous phosphorothioated nucleotides.

In another embodiment, the antisense strand comprises a 5' phosphate moiety. In another embodiment, the antisense strand comprises a moiety R at the 5' end. In an embodiment R is selected from the group consisting of:

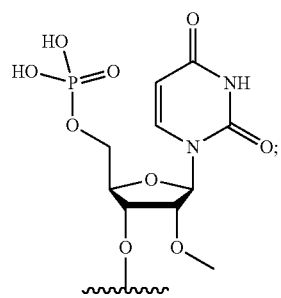

R1

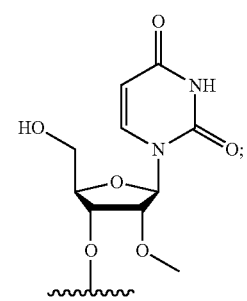

R2

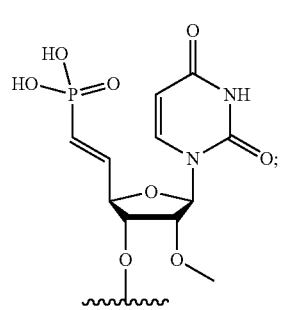

R3

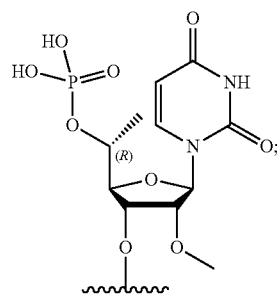

R4

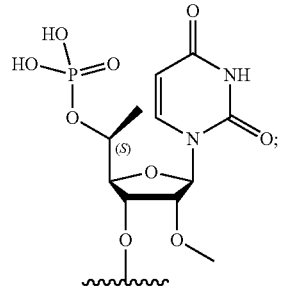

R5

-continued

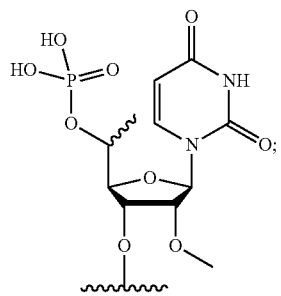

R6

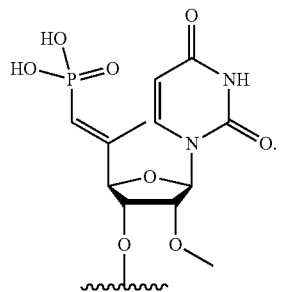

R7

R8

In yet another embodiment, the sense strand and the antisense strand each independently comprises at least 15 contiguous nucleotides.

In yet another embodiment, the sense strand and the antisense strand each independently comprises one or more chemically-modified nucleotides. In another embodiment, the sense strand and the antisense strand each independently consists of chemically-modified nucleotides.

In another embodiment, the sense strand and the antisense strand both comprise alternating 2'-methoxy-nucleotides and 2'-fluoro-nucleotides. In another embodiment, the nucleotides in the region of complementarity in the sense strand are alternating 2'-methoxy-nucleotides and 2'-fluoro-nucleotides, and wherein the nucleotides in the region of complementarity in the antisense strand are alternating 2'-methoxy-nucleotides and 2'-fluoro-nucleotides. In another embodiment, each complementary base pair consists of a 2'-methoxy-nucleotide and a 2'-fluoro-nucleotide. In another embodiment, the overhang regions of the sense strand and the antisense strand independently comprise 2'-methoxy-nucleotides and 2'-fluoro-nucleotides. In another embodiment, the overhang regions of the sense strand and the antisense strand independently consists of at least four consecutive 2'-methoxy-nucleotides. In another embodiment, the overhang regions of the sense strand and the antisense strand consist of 2'-methoxy-nucleotides.

In another embodiment, the nucleotides at positions 1, 2, 3, and 4 from the 3' end of the sense and antisense strands consist of 2'-methoxy-nucleotides. In another embodiment, the nucleotides at positions 1 and 2 of the 5' end of the sense and antisense strands are connected to adjacent nucleotides via phosphorothioate linkages.

In yet another embodiment, the overhang regions of the sense strand and the antisense strand each independently consists of 4, 5, 6, 7, or 8 phosphorothioated nucleotides. In another embodiment, the nucleotides at positions 1-7 or 1-8 from the 3' end of the sense strand or the 3' end of the antisense strand are each connected to adjacent nucleotides via phosphorothioate linkages.

In another embodiment, the overhang regions of the sense strand and the antisense strand have the same number of phosphorothioated nucleotides. In another embodiment, the overhang regions of the sense strand and the antisense strand have different numbers of phosphorothioated nucleotides.

In another embodiment, the overhang region comprises abasic nucleotides.

In yet another embodiment, the structure is selected from Formulas (I-VIII)

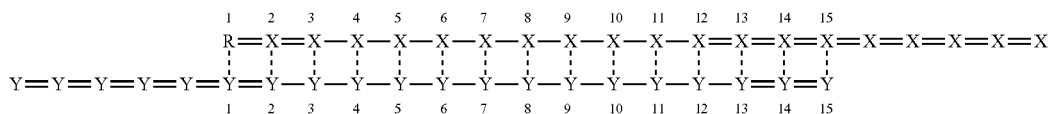

Formula I

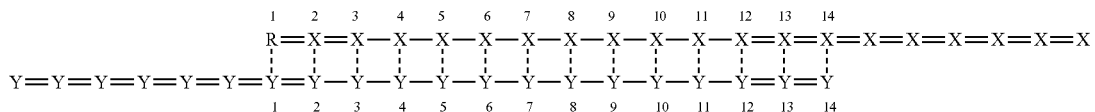

Formula II

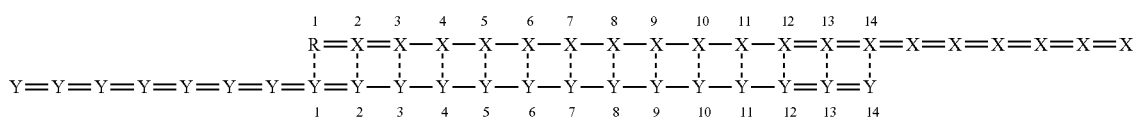

Formula III

Formula IV
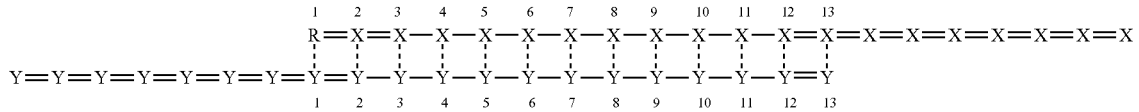

Formula V
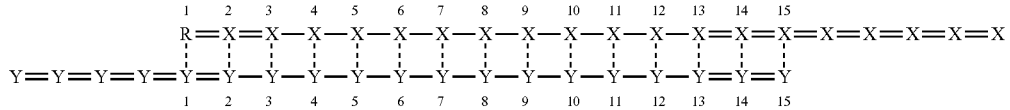

Formula VI
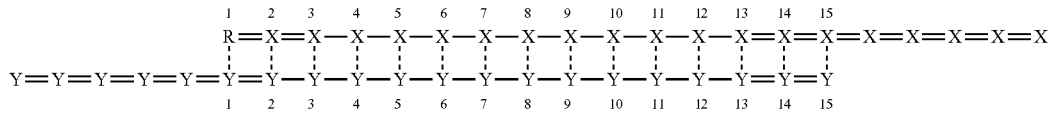

Formula VII
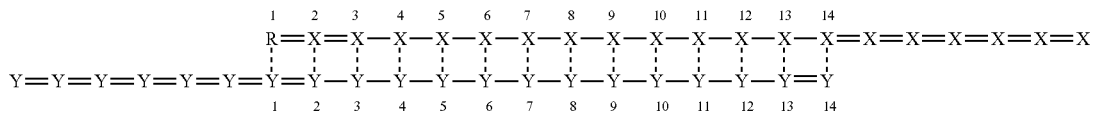

Formula VIII
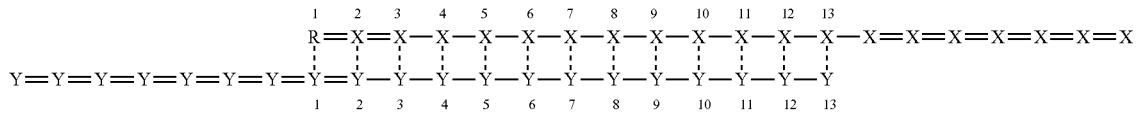

in which, X, for each occurrence, independently, is selected from adenosine, guanosine, uridine, cytidine, and chemically-modified derivatives thereof;
Y, for each occurrence, independently, is selected from adenosine, guanosine, uridine, cytidine, and chemically-modified derivatives thereof;
- represents a phosphodiester internucleoside linkage;
= represents a phosphorothioate internucleoside linkage;
--- represents, individually for each occurrence, a base-pairing interaction or a mismatch; and
R, for each occurrence, is a nucleotide comprising a 5' phosphate or is R1, R2, R3, R4, R5, R6, R7 or R8, as defined above.

In an embodiment of formulas I-VIII, the sense strand and the antisense strand each comprise one or more chemically-modified nucleotides. In another embodiment formulas I-VIII, the sense strand and the antisense strand each consist of chemically-modified nucleotides. In another embodiment formulas I-VIII, the sense strand and the antisense strand independently comprise alternating 2'-methoxy-nucleotides and 2'-fluoro-nucleotides.

In another embodiment, wherein the antisense strand has perfect complementarity to a target. In yet another embodiment, the antisense strand has between 80% and 99% complementarity to a target.

In another aspect, provided herein is a pharmaceutical composition comprising one or more double stranded nucleic acid compounds as described herein, and a pharmaceutically acceptable carrier.

In another aspect, provided herein are methods for treating a disease or disorder comprising administering to a subject in need of such treatment a therapeutically effective amount of a compound or pharmaceutical composition as described herein.

In an embodiment, the disease or disorder is neurological. In an embodiment, the disease or disorder is Huntington's disease. In an embodiment, the subject in need of such treatment is a human.

In another aspect, provided herein is a method for selective in vivo delivery of a compound as described herein to a target organ, tissue or cells, comprising administering the compound to a subject. In an embodiment, the target organ is the brain. In an embodiment, the target cells are primary cortical neurons. In an embodiment, the delivery of the compound is not mediated by lipid formulation.

In an embodiment, the compound is administered by intravenous injection, intraperitoneal injection, intracranial injection, intrathecal injection, intrastriatal injection, or intracerebroventricular injection.

In another aspect, provided herein are methods for treating a neurological disease or disorder comprising administering to a subject in need of such treatment a therapeutically effective amount of a compound or pharmaceutical composition as described herein.

In an embodiment, the double stranded nucleic acid compound has the structure of Formula (I) or Formula (VI). In an embodiment, the double stranded nucleic acid compound has the structure of Formula (IV) or Formula (VII).

In another aspect, provided herein is a method of inhibiting expression of HTT gene in a subject in need thereof, comprising introducing into the subject a nucleic acid compound as described herein.

In yet another aspect, provided herein is a method of treating or managing Huntingtin's disease comprising administering to a patient in need of such a treatment or management a therapeutically effective amount of a nucleic acid compound as described herein.

In an embodiment, the nucleic acid compound is administered to the brain of the patient. In another embodiment, the nucleic acid compound is administered by intrastriatal injection. In another embodiment, the nucleic acid compound is administered by intracerebroventricular injection.

In another embodiment, administering the nucleic acid compound, as described herein, to the brain causes a decrease in HTT mRNA in the striatum. In yet another embodiment, administering the nucleic acid compound, as described herein, to the brain causes a decrease in HTT mRNA in the cortex.

In another aspect, provided herein is a double-stranded nucleic acid compound comprising a sense strand having a 5' end, a 3' end and a region of complementarity with an antisense strand, an antisense strand having a 5' end, a 3' end, a region of complementarity with target RNA, a first overhang region at the 3' end of the sense strand having 7 contiguous phosphorothioated nucleotides, and a second overhang region at the 3' end of the antisense strand having 7 contiguous phosphorothioated nucleotides.

In another aspect, provided herein is a double-stranded nucleic acid compound comprising a sense strand having a 5' end, a 3' end and a region of complementarity with an antisense strand, an antisense strand having a 5' end, a 3' end, a region of complementarity with target RNA, a first overhang region at the 3' end of the sense strand comprising phosphorothioated nucleotides, and a second overhang region at the 3' end of the antisense strand comprising phosphorothioated nucleotides, wherein the nucleotides in the region of complementarity in the sense strand are alternating 2'-methoxy-nucleotides and 2'-fluoro-nucleotides, wherein the nucleotides in the region of complementarity in the antisense strand are alternating 2'-methoxy-nucleotides and 2'-fluoro-nucleotides, and wherein the region of complementarity with an antisense strand is at least 15 nucleotides in length.

The summary described above is non-limiting and other features and advantages of the disclosed compounds and methods will be apparent from the following detailed description and from the claims.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 4A shows a line graph depicting Huntingtin mRNA expression in primary cortical neuron cells following treatment with four different tt-siRNAs at increasing concentrations. FIG. 4B is a line graph showing Huntingtin mRNA expression in primary cortical neurons following treatment with one-tail siRNA or tt-siRNA (7-13-7).

FIG. 9A is a line graph showing Huntingtin mRNA expression in primary cortical neurons one week after treatment with increasing concentrations of either one-tail siRNA or one of three different tt-siRNA. FIG. 9B depicts a line graph showing Huntingtin mRNA expression in primary cortical neurons one week after treatment with increasing concentrations of either one-tail siRNA or four different tt-siRNA.

DETAILED DESCRIPTION

Provided herein are novel two-tailed, chemically modified, double-stranded nucleic acids that are efficacious for in vivo gene silencing. In one aspect, a double-stranded nucleic acid compound comprising (a) a sense strand having a 5' end, a 3' end and a region of complementarity with an antisense strand; (b) an antisense strand having a 5' end, a 3' end and a region of complementarity with the sense strand; (c) an overhang region at the 3' end of the sense strand having at least 3 contiguous phosphorothioated nucleotides; and (d) an overhang region at the 3' end of the antisense strand having at least 3 contiguous phosphorothioated nucleotides is provided.

In an embodiment, the double-stranded nucleic acid compound is a tt-siRNA that does not comprise a second tt-siRNA, wherein both tt-siRNAs are linked to each other at the 3' positions.

In an embodiment, the double-stranded nucleic acid compound does not consist of two tt-siRNAs, linked to each other at the 3' positions via a linker having the structure:

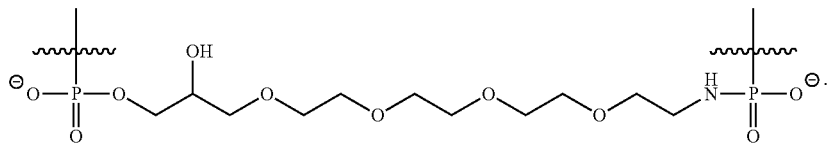 [SMILES: *P(=O)([O-])NCCOCCOCCOCCOCC(O)COP(*)(=O)[O-]]

Figure 13:
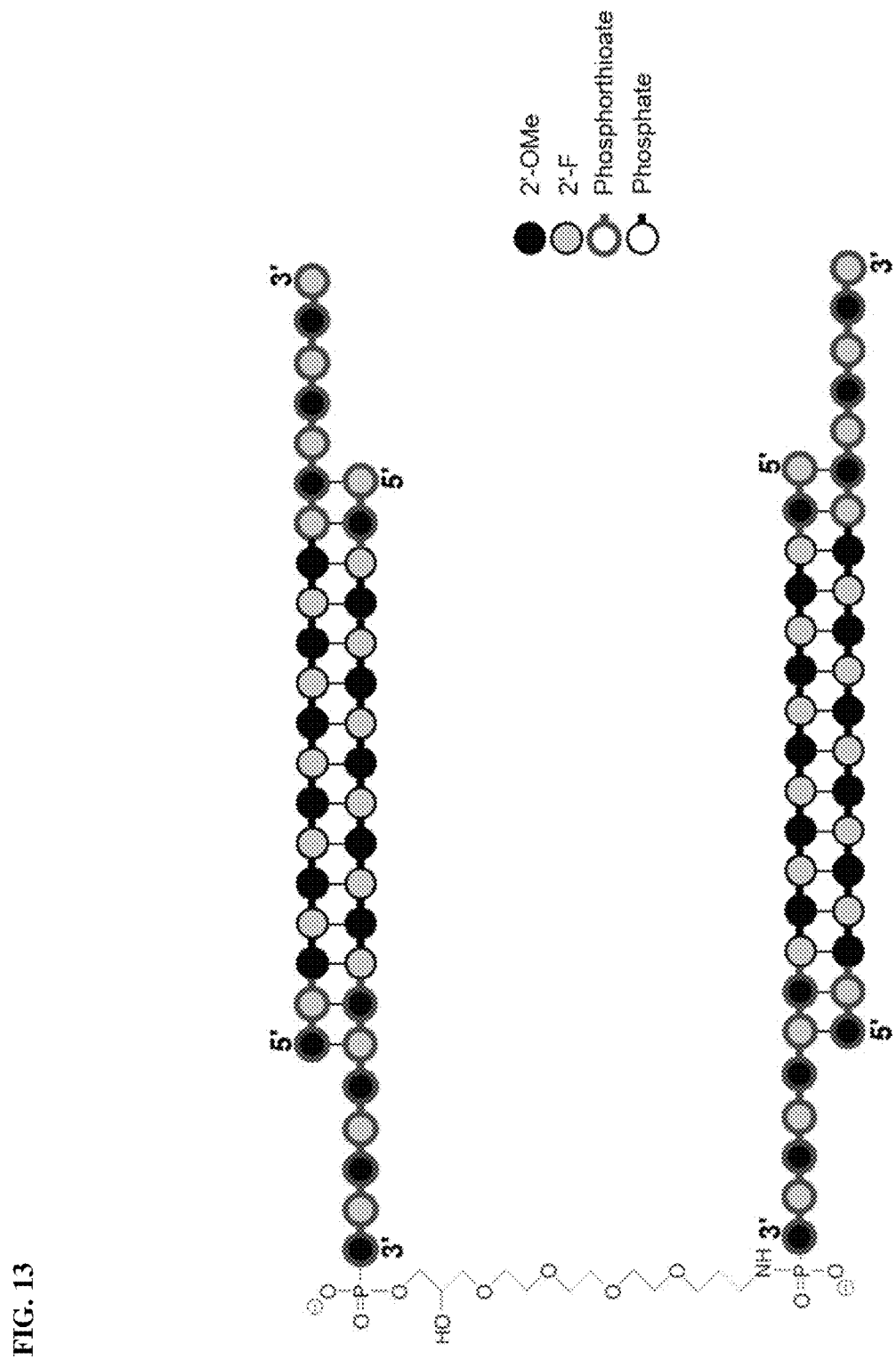
FIG. 13 depicts an asymmetric compound comprising two double-stranded siRNAs.

In an embodiment, the double-stranded nucleic acid compound does not have the structure of the compound depicted in FIG. 13.

In an embodiment, the sense strand and the antisense strand each independently comprise at least 15 contiguous nucleotides. In an embodiment, the sense strand and the antisense strand each independently consist of 18-22 contiguous nucleotides. In an embodiment, the sense strand and the antisense strand each independently consist of at least 20 contiguous nucleotides. In an embodiment, the sense strand and the antisense strand each independently consist of 15, 16, 17, 18, 19, 20, 21, 22, 23, 24 or 25 nucleotides.

In an embodiment, the overhang region of the sense strand has the same number of nucleotides as the overhang region of the antisense strand (i.e., the double-stranded nucleic acid is symmetrical). In an embodiment, the overhang region of the sense strand has a different number of nucleotides as the overhang region of the antisense strand (i.e., the double-stranded nucleic acid is asymmetrical).

In an embodiment, the overhang regions of the sense and antisense strands independently consist of 3, 4, 5, 6, 7, 8, 9 or 10 nucleotides. In an embodiment, the overhang regions of the sense and antisense strands independently consist of 5, 6 or 7 nucleotides. In an embodiment, the overhang regions of the sense and antisense strands both consist of 5, 6 or 7 nucleotides.

The regions of complementarity of the sense and antisense strands of a double stranded nucleic acid compound together constitute the "double-stranded region" of the double-stranded nucleic acid compound. In an embodiment, the double-stranded region is 10, 11, 12, 13, 14, 15, 16, 17 or 18 nucleotides in length (i.e., the regions of complementarity of the sense and antisense strands are 10, 11, 12, 13, 14, 15, 16, 17 or 18 nucleotides in length). In a particular embodiment, the double-stranded region is 13, 14 or 15 nucleotides in length.

In an embodiment, the sense strand and the antisense strand each independently comprises one or more chemically-modified nucleotides. In an embodiment, the sense strand or the antisense strand consists of chemically-modified nucleotides. In an embodiment, the sense strand and the antisense strand each consist of chemically-modified nucleotides.

In an embodiment, the sense strand and the antisense strand both comprise alternating 2'-methoxy-nucleotides and 2'-fluoro-nucleotides. In an embodiment, the nucleotides in the double stranded region in the sense strand are alternating 2'-methoxy-nucleotides and 2'-fluoro-nucleotides, and/or the nucleotides in the double stranded region in the antisense strand are alternating 2'-methoxy-nucleotides and 2'-fluoro-nucleotides.

In an embodiment, each complementary base pair of a double stranded region consists of a 2'-methoxy-nucleotide and a 2'-fluoro-nucleotide.

In an embodiment, the overhang regions of the sense strand and the antisense strand each independently comprises 2'-methoxy-nucleotides and 2'-fluoro-nucleotides. In an embodiment, the overhang regions of the sense strand and the antisense strand consist of 2'-methoxy-nucleotides. In an embodiment, the overhang regions of the sense strand and the antisense strand each independently consists of at least four (e.g., 4, 5, 6, 7 or 8) consecutive 2'-methoxy-nucleotides.

In an embodiment, one or more nucleotides at positions 1-4 (i.e., 1, 2, 3, and 4), 1-5, 1-6 or 1-7 of the 3' end of the sense and antisense strands consist of 2'-methoxy-nucleotides. In an embodiment, the nucleotides at positions 1-4 of the 3' end of the sense and antisense strands consist of 2'-methoxy-nucleotides.

In an embodiment, the nucleotides at one or both of positions 1 and 2 of the 5' end of the sense and antisense strands are connected to adjacent nucleotides via phosphorothioate linkages.

In an embodiment, the overhang region of the sense strand and the antisense strand independently consists of 3, 4, 5, 6, 7, 8, 9 or 10 phosphorothioated nucleotides.

In an embodiment, one or more nucleotides at positions 1-4 (i.e., 1, 2, 3 and 4), 1-5, 1-6, 1-7, 1-8 of the 3' end of the sense strand or the 3' end of the antisense strand, are connected to adjacent nucleotides via phosphorothioate linkages.

In an embodiment, the overhang regions of the sense strand and the antisense strand have the same number of phosphorothioated nucleotides. In an embodiment, the overhang regions of the sense strand and the antisense strand have different numbers of phosphorothioated nucleotides relative to each other.

In an embodiment, the overhang regions of the sense strand and the antisense strand comprise one or more abasic nucleotides. In another embodiment, each nucleotide of the overhang regions is abasic.

In an embodiment, the sense strand of the double-stranded nucleic acid has homology with a target. In a particular embodiment, the sense strand has complete homology with the target.

In an embodiment, the antisense strand of the double-stranded nucleic acid has complementarity with a target. In a particular embodiment, the antisense strand has complete complementarity with the target. In another embodiment, the antisense strand has partial complementarity with a target. In another embodiment, the antisense strand has 95%, 90%, 85%, 80%, 75%, 70%, or 65% complementarity with a target. In an embodiment, the antisense strand has between 80% and 99% complementarity to a target. In a particular embodiment, the target is the HTT gene.

In a particular embodiment, the target mRNA is mammalian or viral mRNA. In another particular embodiment, the target is an intronic region of the target mRNA. In a particular embodiment, the target mRNA is produced by a gene associated with a neurological disorder, e.g., HTT.

In an embodiment, the double-stranded nucleic acid compound has a structure selected from Formulas (I-VIII):

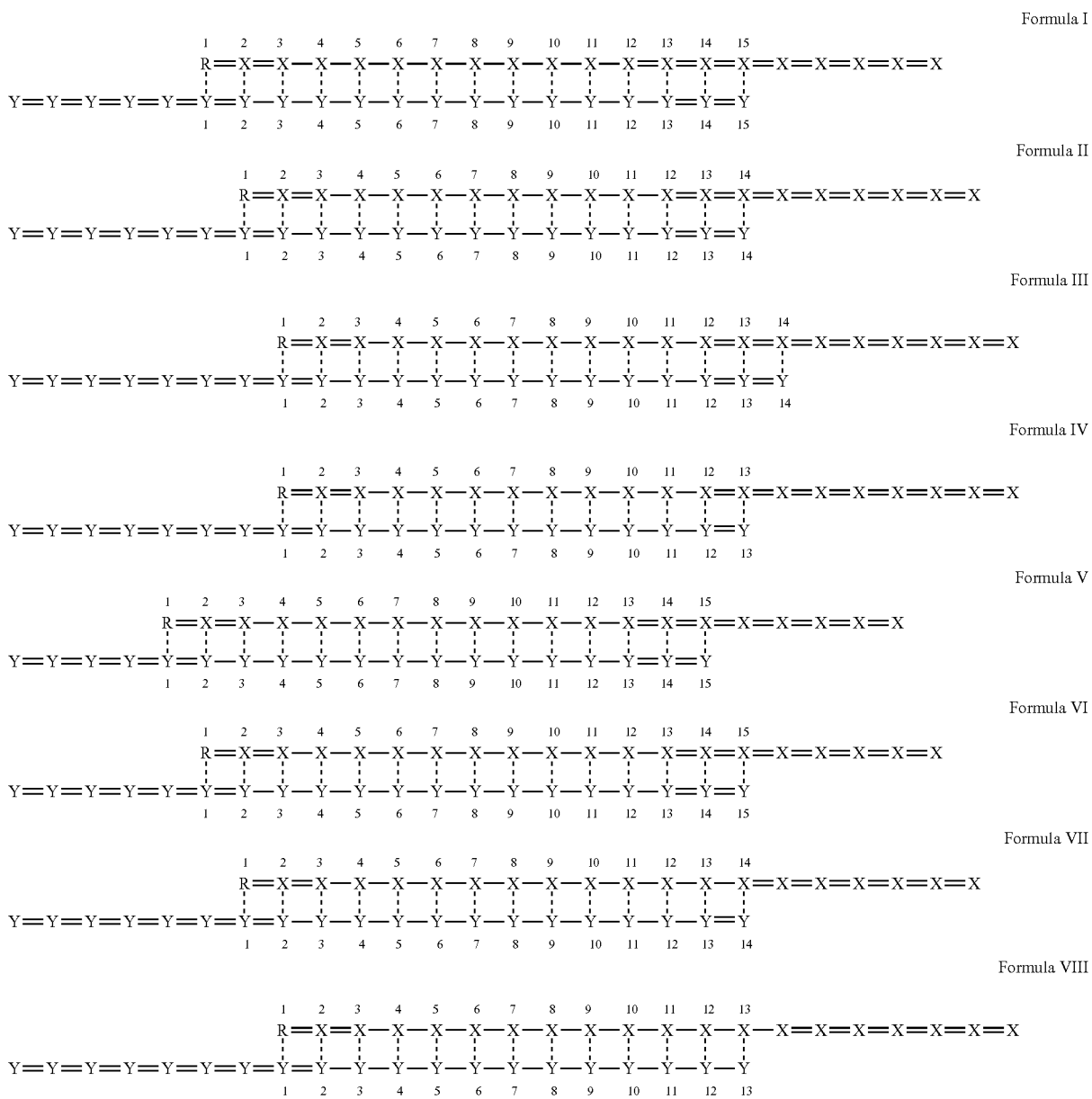

wherein: X, for each occurrence, is independently selected from adenosine, guanosine, uridine, cytidine, and chemically-modified derivatives thereof; Y, for each occurrence, is independently selected from adenosine, guanosine, uridine, cytidine, and chemically-modified derivatives thereof; - represents a phosphodiester internucleoside linkage; = represents a phosphorothioate internucleoside linkage; --- represents, individually for each occurrence, a base-pairing interaction or a mismatch; and R, for each occurrence, is a nucleotide comprising a 5' phosphate or is R1, R2, R3, R4, R5, R6, R7 or R8, as defined above.

In an embodiment, the sense strand and the antisense strand each comprises one or more chemically-modified nucleotides. In an embodiment, the sense strand and the antisense strand each consists of chemically-modified nucleotides. In an embodiment, the sense strand and the antisense strand independently comprise alternating 2'-methoxy-nucleotides and 2'-fluoro-nucleotides. In an exemplary embodiment, the double stranded nucleic acid compound has the structure of Formula (I) or Formula (VI). In another exemplary embodiment, the double stranded nucleic acid compound has the structure of Formula (IV) or Formula (VII). In another aspect, provided herein is a pharmaceutical composition comprising one or more double stranded nucleic acid compounds as described herein, and a pharmaceutically acceptable carrier.

In another aspect, provided herein is a method of treating a disease or disorder comprising administering to a subject in need of such treatment a therapeutically effective amount of a compound or pharmaceutical composition as described herein.

In an embodiment of the method, the disease or disorder is neurological. In an embodiment, the neurological disease is Huntington's disease. In another embodiment, the disease is selected from the group consisting of Alzheimer's disease, frontotemporal dementia, progressive supranuclear palsy, corticobasal dementia, Parkinson's with Lewy-Body dementia, post-traumatic neurodegeneration, and chronic traumatic encephalopathy.

In an embodiment, the subject in need of such treatment is a human. In another embodiment, the subject in need of such treatment is a mouse. In another embodiment, the subject in need of such treatment is a rat. In another embodiment, the subject in need of such treatment is a monkey. In another embodiment, the subject in need of such treatment is a sheep. In another embodiment, the subject in need of such treatment is a dog.

In another aspect, provided herein is a method of treating a neurological disease or disorder comprising administering to a subject in need of such treatment a therapeutically effective amount of a compound or pharmaceutical composition as described herein.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting. As used herein, unless otherwise stated, the singular forms "a," "an," and "the" include plural reference. Thus, for example, a reference to "a protein" includes a plurality of protein molecules.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The term "complementary" refers to the relationship between nucleotides exhibiting Watson-Crick base pairing, or to oligonucleotides that hybridize via Watson-Crick base pairing to form a double-stranded nucleic acid. The term "complementarity" refers to the state of an oligonucleotide (e.g., a sense strand or an antisense strand) that is partially or completely complementary to another oligonucleotide. Oligonucleotides described herein as having complementarity to a second oligonucleotide may be 100%, >95%, >90%, >85%, >80%, >75%, >70%, >65%, >60%, >55% or >50% complementary to the second oligonucleotide.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base cytosine (e.g., cytidine or a chemically-modified derivative thereof).

As used herein, the term "3' end" refers to the end of a nucleic acid that contains an unmodified hydroxyl group at the 3' carbon of its ribose ring.

As used herein, the term "5' end" refers to the end of a nucleic acid that contains a phosphate group attached to the 5' carbon of its ribose ring.

As used herein, the term "nucleoside" refers to a molecule made up of a heterocyclic base and its sugar.

As used herein, the term "nucleotide" refers to a nucleoside having a phosphate group on its 3' or 5' sugar hydroxyl group.

An RNAi agent, e.g., a tt-siRNA, having a strand which is "sequence sufficiently complementary to a target mRNA sequence to direct target-specific RNA interference (RNAi)" means that the strand has a sequence sufficient to trigger the destruction of the target mRNA by RNAi.

As used herein, the term "isolated RNA" (e.g., "isolated tt-siRNA," "isolated siRNA" or "isolated siRNA precursor") refers to an RNA molecule that is substantially free of other cellular material, or culture medium when produced by recombinant techniques, or substantially free of chemical precursors or other chemicals when chemically synthesized.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

As used herein, the term "siRNA" refers to small interfering RNAs that induce the RNA interference (RNAi) pathway. siRNA molecules can vary in length (generally between 18-30 basepairs) and contain varying degrees of complementarity to their target mRNA. The term "siRNA" includes duplexes of two separate strands, as well as single strands that can form hairpin structures comprising a duplex region.

As used herein, the term "antisense strand" refers to the strand of an siRNA duplex that contains some degree of complementarity to a target gene or mRNA and contains complementarity to the sense strand of the siRNA duplex.

As used herein, the term "sense strand" refers to the strand of an siRNA duplex that contains complementarity to the antisense strand of the siRNA duplex.

As used herein, the term "overhang" or "tail" refers to 3, 4, 5, 6, 7, 8, 9, 10, 11, 12, 13, 14, 15, 16, 17, 18, 19, 20 or more sequential nucleotides at the 3' end of one or both of the sense strand and the antisense strand that are single-stranded, i.e., are not base paired to (i.e., do not form a duplex with) the other strand of the siRNA duplex.

As used herein, the term "two-tailed oligonucleotide" or "tt-siRNA" refers to a double-stranded siRNA that comprises a sense strand and an antisense strand, a duplex region where the sense strand and the antisense strands are base-paired, and one overhanging, single-stranded tail located at each of the 3' end of the sense strand and the 3' end of the antisense strand. Each of the single-stranded tails independently comprises three, four, five, six, seven, eight or more overhanging nucleotides that do not form a duplex with nucleotides from the other strand. Each of the overhanging, single-stranded tails of a tt-siRNA comprises or consists of phosphorothioated nucleotides.

In certain exemplary embodiments, a tt-siRNA of the invention comprises a duplex region of between about 8-20 nucleotides or nucleotide analogs in length, between about 10-18 nucleotides or nucleotide analogs in length, between about 12-16 nucleotides or nucleotide analogs in length, or between about 13-15 nucleotides or nucleotide analogs in length (e.g., a duplex region of about 8, 9, 10, 11, 12, 13, 14, 15, 16, 17, 18, 19 or 20 base pairs).

In certain exemplary embodiments, each overhang of the tt-siRNA of the invention comprises at least about 3, about 4, about 5, about 6, about 7, about 8, about 9, or about 10 sequential nucleotides. In certain embodiments, each overhang of the tt-siRNA of the invention is about 4, about 5, about 6 or about 7 nucleotides in length. In certain embodiments, the sense strand overhang is the same number of nucleotides in length as the antisense strand overhang. In other embodiments, the sense strand overhang has fewer nucleotides than the antisense strand overhang. In other embodiments, the antisense strand overhang has fewer nucleotides than the sense strand overhang.

In certain exemplary embodiments, a tt-siRNA of the invention comprises a sense strand and/or an antisense strand each having a length of about 10, about 15, about 20, about 25 or about 30 nucleotides. In particular embodiments, a tt-siRNA of the invention comprises a sense strand and/or an antisense strand each having a length of between about 15 and about 25 nucleotides. In particular embodiments, a tt-siRNA of the invention comprises a sense strand and an antisense strand that are each about 20 nucleotides in length. In certain embodiments, the sense strand and the antisense strand of a tt-siRNA are the same length. In other embodiments, the sense strand and the antisense strand of a tt-siRNA are different lengths.

In certain exemplary embodiments, a tt-siRNA of the invention has a total length (from the 3' end of the antisense strand to the 3' end of the sense strand) of about 20, about 25, about 30, about 35, about 40, about 45, about 50 or about 75 nucleotides. In certain exemplary embodiments, a tt-siRNA of the invention has a total length of between about 15 and about 35 nucleotide. In other exemplary embodiments, the tt-siRNA of the invention has a total length of between about 20 and about 30 nucleotides. In other exemplary embodiments, the tt-siRNA of the invention has a total length of between about 22 and about 28 nucleotides. In particular embodiments, a tt-siRNA of the invention has a total length of about 20, about 21, about 22, about 23, about 24, about 25, about 26, about 27, about 28, about 29 or about 30 nucleotides.

As used herein, the terms "chemically modified nucleotide" or "nucleotide analog" or "altered nucleotide" or "modified nucleotide" refer to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10 (4):297-310.

Nucleotide analogs may also comprise modifications to the sugar portion of the nucleotides. For example the 2' OH-group may be replaced by a group selected from H, OR, R, F, Cl, Br, I, SH, SR, NH2, NHR, NR$_2$, COOR, or OR, wherein R is substituted or unsubstituted C1-C6 alkyl, alkenyl, alkynyl, aryl, etc. Other possible modifications include those described in U.S. Pat. Nos. 5,858,988, and 6,291,438.

As used herein, the term "metabolically stabilized" refers to RNA molecules that contain ribonucleotides that have been chemically modified from 2'-hydroxyl groups to 2'-O-methyl groups. In particular embodiments, the duplex region of a tt-siRNA comprises one or more 2'-fluoro modifications and/or one or more 2'-methoxy modifications. In certain exemplary embodiments, the duplex region comprises alternating 2'-fluoro modifications and alternating 2'-methoxy modifications in one or both of the sense strand and the antisense strand.

As used herein, the term "phosphorothioate" refers to the phosphate group of a nucleotide that is modified by substituting one or more of the oxygens of the phosphate group with sulfur. A phosphorothioate further comprises a cationic counter-ion (e.g., sodium, potassium, calcium, magnesium or the like). The term "phosphorothioated nucleotide" refers to a nucleotide having one or two phosphorothioate linkages to another nucleotide. In certain embodiments, the single-stranded tails of the tt-siRNAs of the invention comprise or consist of phosphorothioated nucleotides.

Figure 12:
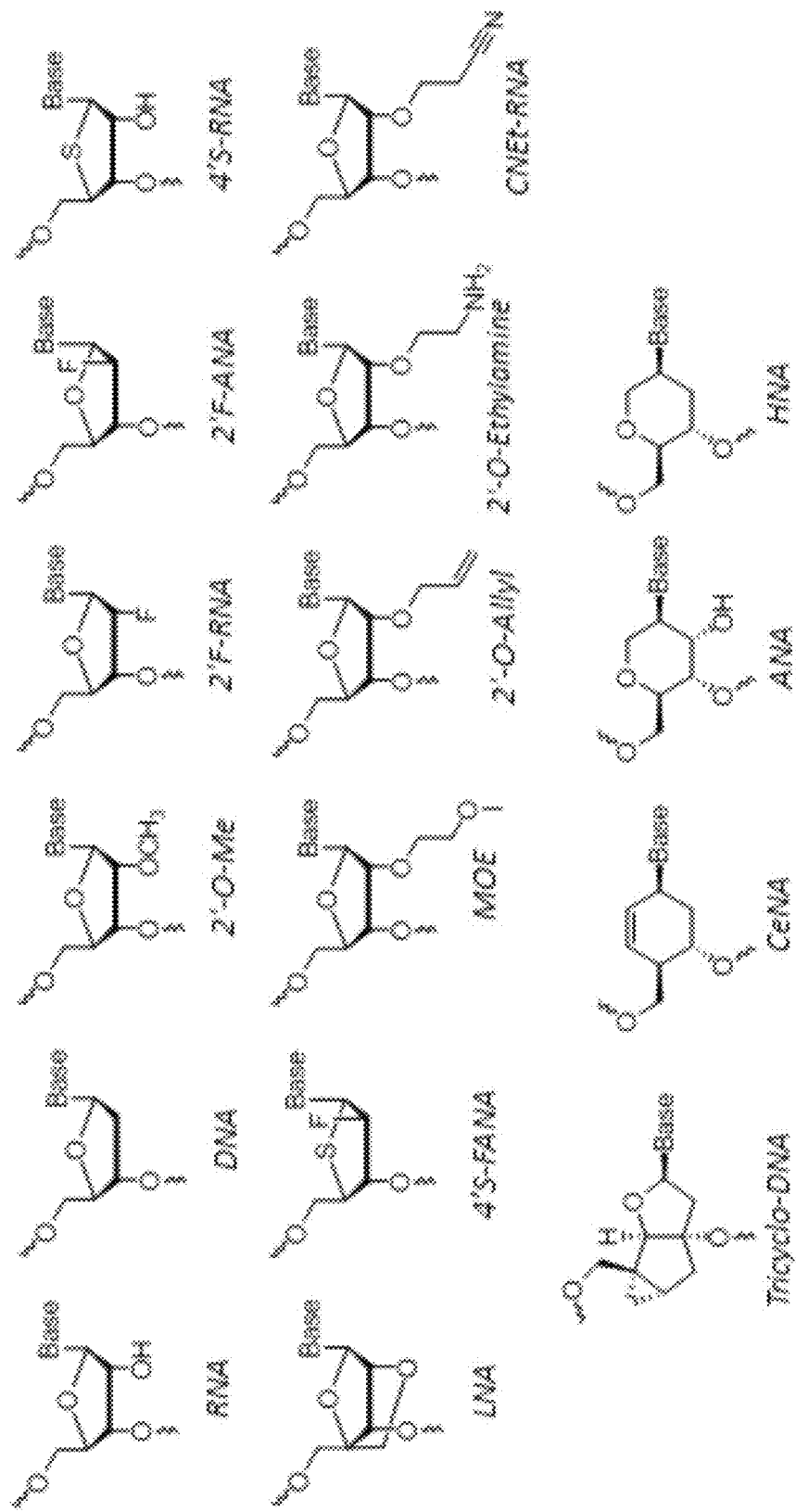
FIG. 12 depicts sugar modifications of two-tailed siRNAs according to certain exemplified embodiments.

In some embodiments, the compounds, oligonucleotides and nucleic acids described herein may be modified to comprise one or more internucleotide linkages provided in FIG. 12. In particular embodiments, the compounds, oligonucleotides and nucleic acids described herein comprise one or more internucleotide linkages selected from phosphodiester and phosphorothioate.

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

Figure 11:
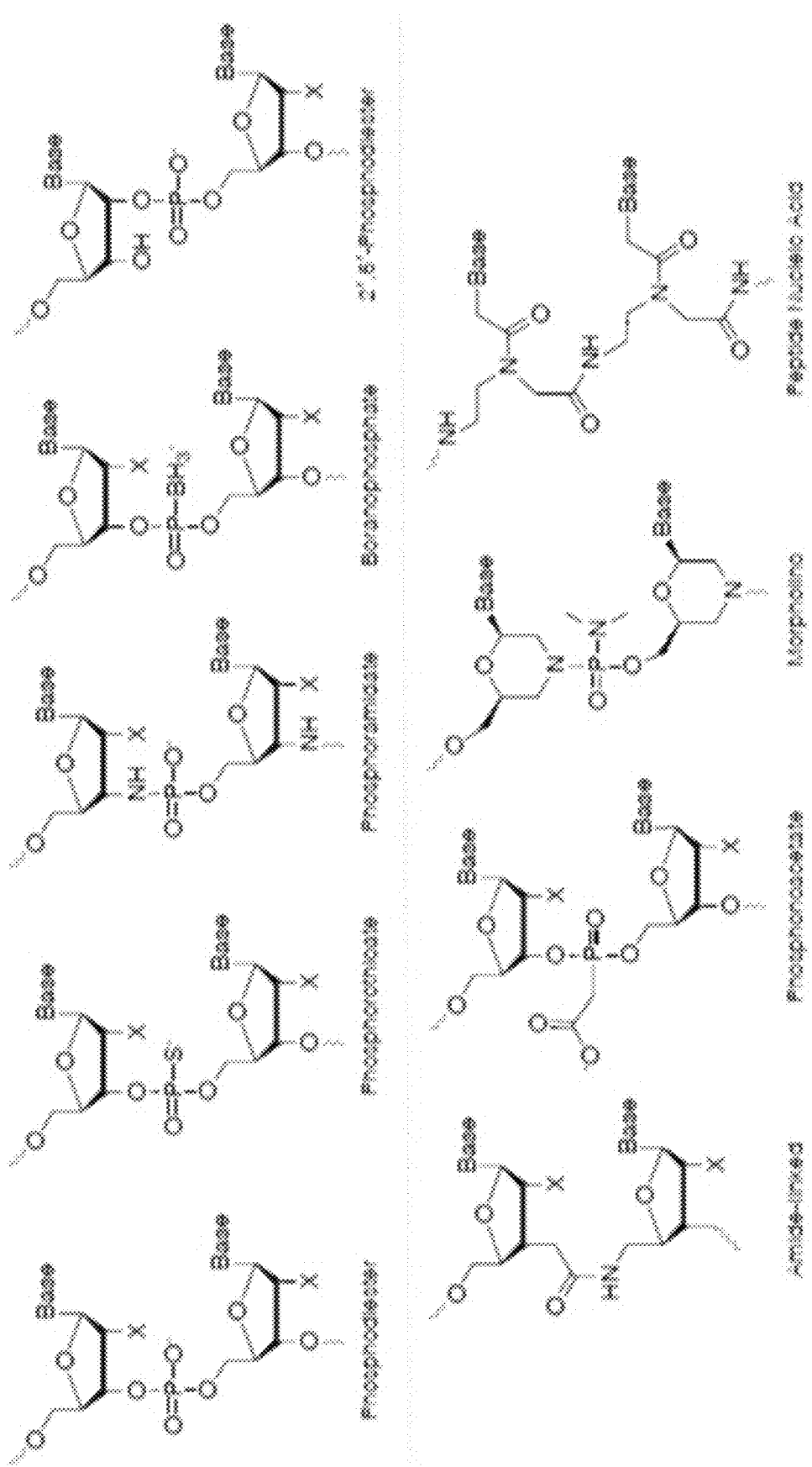
FIG. 11 depicts backbone linkages of two-tailed siRNAs according to certain exemplified embodiments.

In some embodiments, the compounds, oligonucleotides and nucleic acids described herein may be modified to comprise one or more internucleotide backbone linkages provided in FIG. 11.

As used herein, the term "lipid formulation" may refer to liposomal formulations, e.g., wherein liposomes are used to form aggregates with nucleic acids in order to promote penetration of the nucleic acids into a cell. Without being bound by theory, liposomes are useful for penetration into a cell because the phospholipid bilayer readily merges with the phospholipid bilayer of the cell membrane, thereby allowing the nucleic acids to penetrate the cell.

In some embodiments, the compounds, oligonucleotides and nucleic acids described herein may be modified to comprise one or more internucleotide linkages provided in FIG. 12. In particular embodiments, the compounds, oligonucleotides and nucleic acids described herein comprise one or more internucleotide linkages selected from phosphodiester and phosphorothioate.

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

siRNA Design

In some embodiments, a tt-siRNA molecule of the invention is a duplex consisting of a sense strand and complementary antisense strand, the antisense strand having sufficient complementary to an htt mRNA to mediate RNAi. In certain exemplary embodiments, the tt-siRNA molecule has a length from about 10-50 or more nucleotides, i.e., each strand comprises 10-50 nucleotides (or nucleotide analogs or combinations of nucleotides and nucleotide analogs). In other exemplary embodiments, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region to mediate RNAi. In certain exemplary embodiments, the strands are aligned such that there are at least 4, 5, 6, 7, 8, 9, 10 or more bases at the end of the strands do not align (i.e., for which no complementary bases occur in the opposing strand) such that an overhang of 4, 5, 6, 7, 8, 9, 10 or more residues occurs at each of or both ends of the duplex when strands are annealed. In certain exemplary embodiments, the siRNA molecule has a length from about 10-50 or more nucleotides, i.e., each strand comprises 10-50 nucleotides (or nucleotide analogs or combinations of nucleotides and nucleotide analogs). In particularly exemplary embodiments, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, tt-siRNAs can be designed by using any method known in the art, for instance, by using the following protocol:

1. The tt-siRNA should be specific for a target sequence. The first strand should be complementary to the target sequence, and the other strand is substantially complementary to the first strand. In one embodiment, the target sequence is outside the expanded CAG repeat of the mutant htt allele. In another embodiment, the target sequence is outside a coding region of the htt allele. Exemplary target sequences are selected from the 5' untranslated region (5'-UTR) or an intronic region of a target gene. Cleavage of mRNA at these sites should eliminate translation of corresponding mutant protein. Target sequences from other regions of the htt gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the tt-siRNA is designed based on the sequence of the selected target site. In certain exemplary embodiments, the sense strand includes about 19 to 25 nucleotides, e.g., 19, 20, 21, 22, 23, 24 or 25 nucleotides. In particularly exemplary embodiments, the sense strand includes 19, 20 or 21 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. In certain exemplary embodiments, the RNA silencing agents of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The tt-siRNA molecules of the invention have sufficient complementarity with the target sequence such that the tt-siRNA can mediate RNAi. In general, tt-siRNA containing nucleotide sequences sufficiently identical to a target sequence portion of the target gene to effect RISC-mediated cleavage of the target gene are particularly suitable. Accordingly, in an exemplary embodiment, the sense strand of the tt-siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is particularly suitable. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., percent (%) homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). An exemplary, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). An exemplary non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the tt-siRNA is routinely the same length as the sense strand and includes complementary nucleotides. In one embodiment, the strands of the siRNA are paired in such a way as to have a 3' overhang of 4 to 15, e.g., 4, 5, 6 or 7 nucleotides.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of tt-siRNA may be found in "The siRNA User Guide," available at The Max-Plank-Institut fur Biophysikalishe Chemie website.

Alternatively, the tt-siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional exemplary hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm(°C.)=2(\# \text{ of A+T bases})+4(\# \text{ of G+C bases})$. For hybrids between 18 and 49 base pairs in length, $Tm(°C.)=81.5+16.6(\log 10[Na+])+0.41(\% \text{ G+C})-(600/N)$, where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control tt-siRNA should have the same nucleotide composition as the selected tt-siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control tt-siRNAs can be designed by introducing one or more base mismatches into the sequence.

6. To validate the effectiveness by which siRNAs destroy target mRNAs (e.g., wild-type or mutant huntingtin mRNA), the siRNA may be incubated with target cDNA (e.g., huntingtin cDNA) in a Drosophila-based in vitro mRNA expression system. Radiolabeled with $^{32}P$, newly synthesized target mRNAs (e.g., huntingtin mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected tt-siRNA. A homology search can be performed to ensure that the negative control lacks homology to any other gene in the appropriate genome. In addition, negative control tt-siRNAs can be designed by introducing one or more base mismatches into the sequence.

Modified Nucleotides

In an embodiment, a tt-siRNA comprises one or more chemically-modified nucleotides. In an embodiment, a two-tailed oligonucleotide consists of chemically-modified nucleotides. In certain embodiments of a two-tailed oligonucleotide, >95%, >90%, >85%, >80%, >75%, >70%, >65%, >60%, >55% or >50% of the nucleic acid comprises chemically-modified nucleotides.

In an embodiment, the sense strand and the antisense strand of the tt-siRNA each comprises one or more chemically-modified nucleotides. In an embodiment, each nucleotide of the sense strand and the antisense strand is chemically-modified. In an embodiment, the sense strand and the antisense strand both comprise alternating 2'-methoxy-nucleotides and 2'-fluoro-nucleotides. In an embodiment, the nucleotides at positions 1 and 2 of the 5' end of the sense and antisense strands are connected to adjacent nucleotides via phosphorothioate linkages. In an embodiment, the nucleotides at positions 1-6 of the 3' end, or positions 1-7 of the 3' end, are connected to adjacent nucleotides via phosphorothioate linkages. In other embodiments, at least 5 nucleotides at the 3' end are connected to adjacent nucleotides via phosphorothioate linkages.

Delivery and Distribution

In another aspect, provided herein is a method for selectively delivering a nucleic acid as described herein to a particular organ in a patient, comprising administering to the patient a two-tailed siRNA as described herein, such that the two-tailed siRNA is delivered selectively. In one embodiment, the organ is the liver. In another embodiment, the organ is the kidneys. In another embodiment, the organ is the spleen. In another embodiment, the organ is the heart. In another embodiment, the organ is the brain.

The compositions described herein promote simple, efficient, non-toxic delivery of metabolically stable two-tailed siRNAs, and promote potent silencing of therapeutic targets in a range of tissues in vivo.

In another aspect, provided herein is a method for selective in vivo delivery of a compound as described herein to a target organ, tissue or cells, comprising administering the compound to a subject. In an embodiment, the target organ is the brain. In an embodiment, the target cells are primary cortical neurons. In an embodiment, the delivery of the compound is not mediated by lipid formulation.

In an embodiment, the method is at least 50%, at least 60%, at least 70%, at least 80%, at least 90% or at least 99% selective to the target organ, i.e., at least 50%, at least 60%, at least 70%, at least 80%, at least 90% or at least 99% of the tt-siRNA administered to a subject locates to the target organ.

In certain exemplary embodiments, the compound or pharmaceutical composition is administered by intravenous injection, intraperitoneal injection, intracranial injection, intrathecal injection, intrastriatal injection, or intracerebroventricular injection. In a particular embodiment, the compound or pharmaceutical composition is administered by intracerebroventricular injection.

Synthetic tt-siRNAs can be delivered into cells by methods known in the art, including cationic liposome transfection and electroporation. To obtain longer term suppression of the target genes (i.e., htt genes) and to facilitate delivery under certain circumstances, one or more tt-siRNAs can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002), supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when cotransfected into the cells with a vector expressing T7 RNA polymerase (Jacque et al., 2002, supra). A single construct may contain multiple sequences coding for siRNAs, such as multiple regions of the gene encoding htt, targeting the same gene or multiple genes, and can be driven, for example, by separate PolIII promoter sites.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., into neural cells (e.g., brain cells) (US Patent Applications 2014/0296486, 2010/0186103, 2008/0269149, 2006/0078542 and 2005/0220766).

Modified tt-siRNAs

In certain aspects of the invention, an RNA silencing agent (or any portion thereof), e.g., a tt-siRNA, of the invention as described herein may be modified such that the activity of the RNA silencing agent is further improved. For example, the RNA silencing agents described above may be modified with any of the modifications described herein. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the tt-siRNAs of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the tt-siRNA for a non-target mRNA (e.g. wild-type mRNA), without appreciably affecting the specificity of the tt-siRNA for a target mRNA (e.g. gain-of-function mutant mRNA).

In certain exemplary embodiments, the tt-siRNAs of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is particularly suitable because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholine-inosine, LNA-inosine, phosphoramidate-inosine, 2'-O-methoxyethyl-inosine, and 2'-OMe-inosine. In particularly exemplary embodiments, the universal nucleotide is an inosine residue or a naturally occurring analog thereof.

In certain embodiments, the tt-siRNAs of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. tt-siRNAs and shRNAs), the destabilizing nucleotide may be introduced in the strand or strand portion that does not contain the specificity-determining nucleotide. In certain exemplary embodiments, the destabilizing nucleotide is introduced in the same strand or strand portion that contains the specificity-determining nucleotide.

2) Modifications to Enhance Efficacy and Specificity

In certain embodiments, the tt-siRNAs of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. In particular embodiments, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of a tt-siRNA of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. In certain exemplary embodiments, the mismatched base pair is selected from the group consisting of G:A, C:A, C:U, G:G, A:A, C:C and U:U. In other embodiments, the asymmetry of a tt-siRNA of the invention may be enhanced such that there is at least one wobble base pair, e.g., G:U, between the 5' end of the first or antisense strand and the 3' end of the sense strand portion. In other embodiments, the asymmetry of an RNA silencing agent of the invention may be enhanced such that there is at least one base pair comprising a rare nucleotide, e.g., inosine (I). In certain exemplary embodiments, the base pair is selected from the group consisting of an I:A, I:U and I:C. In yet another embodiment, the asymmetry of a tt-siRNA of the invention may be enhanced such that there is at least one base pair comprising a modified nucleotide. In certain exemplary embodiments, the modified nucleotide is selected from the group consisting of 2-amino-G, 2-amino-A, 2,6-diamino-G, and 2,6-diamino-A.

3) tt-siRNAs with Enhanced Stability

The tt-siRNAs of the present invention can be further modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In an exemplary aspect, the invention features tt-siRNAs that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In an exemplary embodiment of the present invention, the tt-siRNAs may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particular exemplary modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include deoxy-abasic, inosine, N3-methyl-uridine, N6, N6-dimethyl-adenosine, pseudouridine, purine ribonucleoside and ribavirin. In certain exemplary embodiments, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O,4'-C-ethylene-bridged nucleic acids, with possible modifications such as 2'-deoxy-2''-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also exemplified are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (in particular embodiments sequence changes are located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, a compound of the invention may be modified with chemical moieties, for example, to enhance cellular uptake by target cells (e.g., neuronal cells). Thus, the invention includes tt-siRNAs which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, a tt-siRNA is conjugated to a lipophilic moiety. In one embodiment, the lipophilic moiety is a ligand that includes a cationic group. In another embodiment, the lipophilic moiety is attached to one or both strands of a tt-siRNA. In an exemplary embodiment, the lipophilic moiety is attached to one end of the sense strand of the tt-siRNA. In another exemplary embodiment, the lipophilic moiety is attached to the 3' end of the sense strand. In certain embodiments, the lipophilic moiety is selected from the group consisting of cholesterol, vitamin D, DHA, DHAg2, EPA, vitamin E, vitamin K, vitamin A, folic acid, or a cationic dye (e.g., Cy3).

Pharmaceutical Compositions and Methods of Administration

In one aspect, provided herein is a pharmaceutical composition comprising a therapeutically effective amount of one or more two-tailed siRNA compounds as described herein, and a pharmaceutically acceptable carrier. In another particular embodiment, the pharmaceutical composition comprises a compound of Formula I-VIII as described herein, and a pharmaceutically acceptable carrier.

The invention pertains to uses of the above-described agents for prophylactic and/or therapeutic treatments as described herein. Accordingly, the modulators (e.g., tt-siRNA agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are particularly suitable. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies typically within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Methods of Treatment

In one aspect, the present invention provides for both prophylactic and therapeutic methods of treating a subject at risk of (or susceptible to) a disease or disorder. In one embodiment, the disease or disorder is a neurological disease or disorder. In a particular embodiment, the disease or disorder is Huntington's disease.

In another aspect, the present invention provides for both prophylactic and therapeutic methods of treating a subject at risk of (or susceptible to) a disease or disorder caused, in whole or in part, by a gain of function mutant protein. In one embodiment, the disease or disorder is a trinucleotide repeat disease or disorder. In another embodiment, the disease or disorder is a polyglutamine disorder. In certain exemplary embodiments, the disease or disorder is a disorder associated with the expression of huntingtin and in which alteration of huntingtin, especially the amplification of CAG repeat copy number, leads to a defect in huntingtin gene (structure or function) or huntingtin protein (structure or function or expression), such that clinical manifestations include those seen in Huntington's disease patients.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a tt-siRNA or vector or transgene encoding same) that is specific for one or more target sequences within the gene, such that sequence specific interference with the gene is achieved. These methods can be performed in vitro (e.g., by culturing the cell with the agent) or, alternatively, in vivo (e.g., by administering the agent to a subject).

A tt-siRNA modified for enhanced uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmol of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly suitable dosages are less than 2, 1, or 0.1 mg/kg of body weight.

Delivery of a tt-siRNA directly to an organ (e.g., directly to the brain, spinal column or the like) can be at a dosage on the order of about 0.00001 mg to about 3 mg per organ, or about 0.0001-0.001 mg per organ, about 0.03-3.0 mg per organ, about 0.1-3.0 mg per eye or about 0.3-3.0 mg per organ. The dosage can be an amount effective to treat or prevent a neurological disease or disorder (e.g., Huntington's disease). In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of a tt-siRNA. The maintenance dose or doses are generally lower than the initial dose, e.g., one-half less of the initial dose. A maintenance regimen can include treating the subject with a dose or doses ranging from 0.01 μg to 1.4 mg/kg of body weight per day, e.g., 10, 1, 0.1, 0.01, 0.001, or 0.00001 mg per kg of bodyweight per day. The maintenance doses are typically administered no more than once every 5, 10, or 30 days. Further, the treatment regimen may last for a period of time which will vary depending upon the nature of the particular disease, its severity and the overall condition of the patient. In certain exemplary embodiments, the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it may be desirable to have the patient undergo maintenance therapy to prevent the recurrence of the disease state, wherein the compound of the invention is administered in maintenance doses, ranging from 0.01 μg to 100 g per kg of body weight (see U.S. Pat. No. 6,107,094).

In another aspect, provided herein is a method of treating or managing Huntington's disease comprising administering to a patient in need of such treatment or management a therapeutically effective amount of a compound, siRNA, or nucleic acid as described herein, or a pharmaceutical composition comprising said compound, siRNA, or nucleic acid.

In certain exemplary embodiments, a composition that includes an RNA silencing agent of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. An exemplary route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the invention is delivered across the Blood-Brain-Barrier (BBB) suing a variety of suitable compositions and methods described herein.

The route of delivery can be dependent on the disorder of the patient. For example, a subject diagnosed with Huntington's disease can be administered a tt-siRNA of the invention directly into the brain (e.g., into the globus pallidus or the corpus striatum of the basal ganglia, and near the medium spiny neurons of the corpus striatum). In addition to a tt-siRNA of the invention, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). For the treatment of Huntington's disease, for example, symptomatic therapies can include the drugs haloperidol, carbamazepine, or valproate. Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

A tt-siRNA of the invention can be further modified such that it is capable of traversing the blood brain barrier (BBB). For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the invention. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29 (4):341-5. doi: 10.1038/nbt.1807; El-Andaloussi S, Lee Y, Lakhal-Littleton S, Li J, Seow Y, Gardiner C, Alvarez-Erviti L, Sargent I L, Wood M J.(2011). Exosome-mediated delivery of siRNA in vitro and in vivo. Nat Protoc. 2012 December; 7 (12):2112-26. doi: 10.1038/nprot.2012.131; E L Andaloussi S, Mäger I, Breakefield X O, Wood M J. (2013). Extracellular vesicles: biology and emerging therapeutic opportunities. Nat Rev Drug Discov. 2013 May; 12 (5):347-57. doi: 10.1038/nrd3978; El Andaloussi S, Lakhal S, Mager I, Wood M J. (2013). Exosomes for targeted siRNA delivery across biological barriers. Adv. Drug Deliv Rev. 2013 March; 65(3):391-7. doi: 10.1016/j.addr.2012.08.008).

In certain embodiments, one or more lipophilic molecules are used to allow delivery of an RNA silencing agent of the invention past the BBB (Alvarez-Ervit (2011)). The RNA silencing agent would then be activated, e.g., by enzyme degradation of the lipophilic disguise to release the drug into its active form.

In certain embodiments, one or more receptor-mediated permeablizing compounds can be used to increase the permeability of the BBB to allow delivery of an RNA silencing agent of the invention. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA silencing agent of the invention across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA silencing agent of the invention can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the invention can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration typically do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

A tt-siRNA of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are particularly suitable. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A particularly suitable group of carbohydrates includes lactose, trehalose, raffinose maltodextrins, and mannitol. Suitable polypeptides include aspartame. Amino acids include alanine and glycine, with glycine being preferred.

pH adjusters or buffers include organic salts prepared from organic acids and bases, such as sodium citrate, sodium ascorbate, and the like; sodium citrate is preferred.

An RNA silencing agent of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier. It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by M R Green and J. Sambrook and Harlow et al., Antibodies: A Laboratory Manual, Chapter 14, Cold Spring Harbor Laboratory, Cold Spring Harbor (2013, 2nd edition).

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1

Synthesis of Two-Tailed siRNAs

Figure 2:
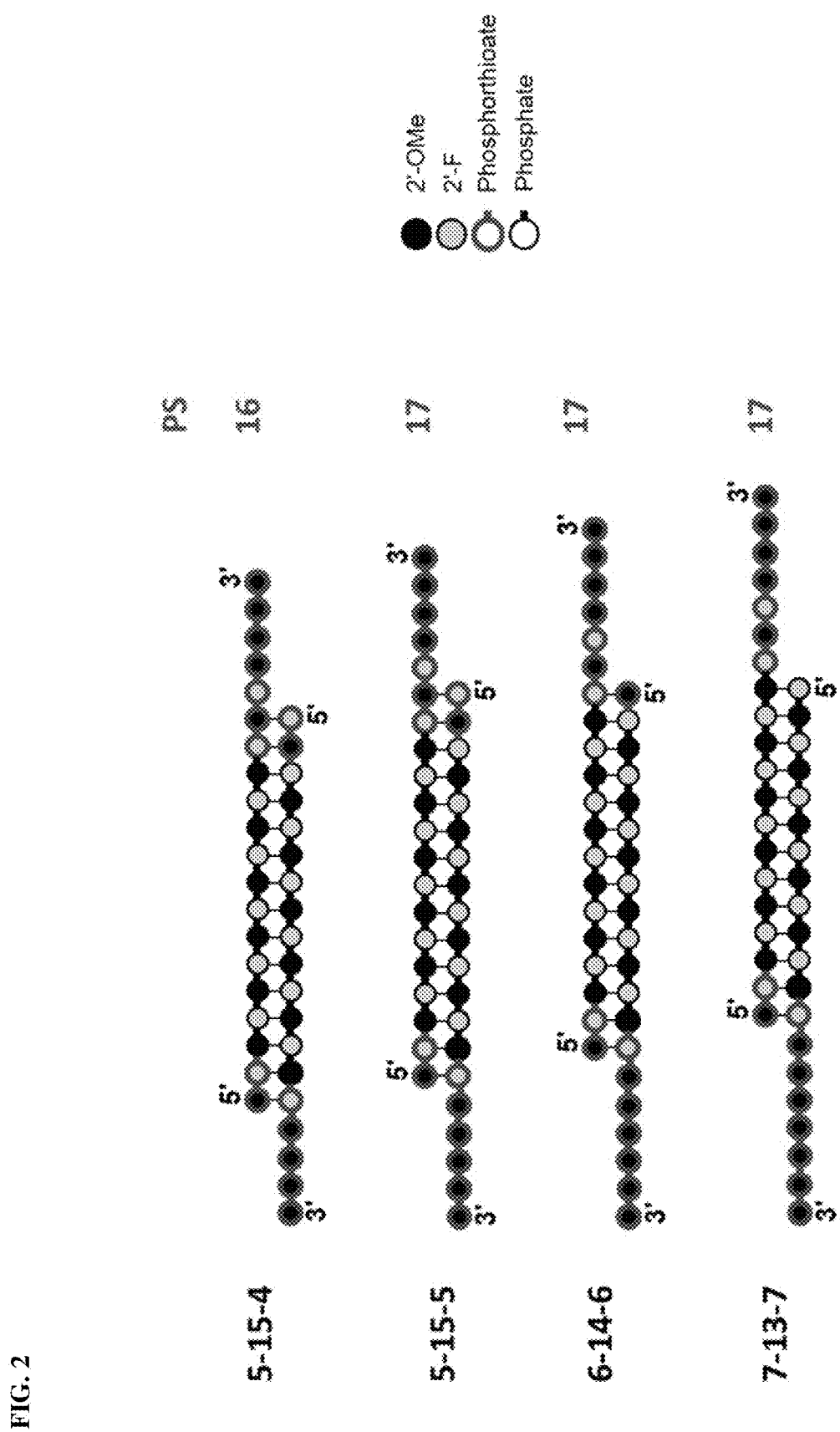
FIG. 2 depicts four examples of two-tailed siRNAs (tt-siRNAs) having phosphorothioated tails with differing lengths while maintaining the same number of total phosphorothioates. In all cases the antisense strand has a chemically attached 5' phosphate.
Figure 5:
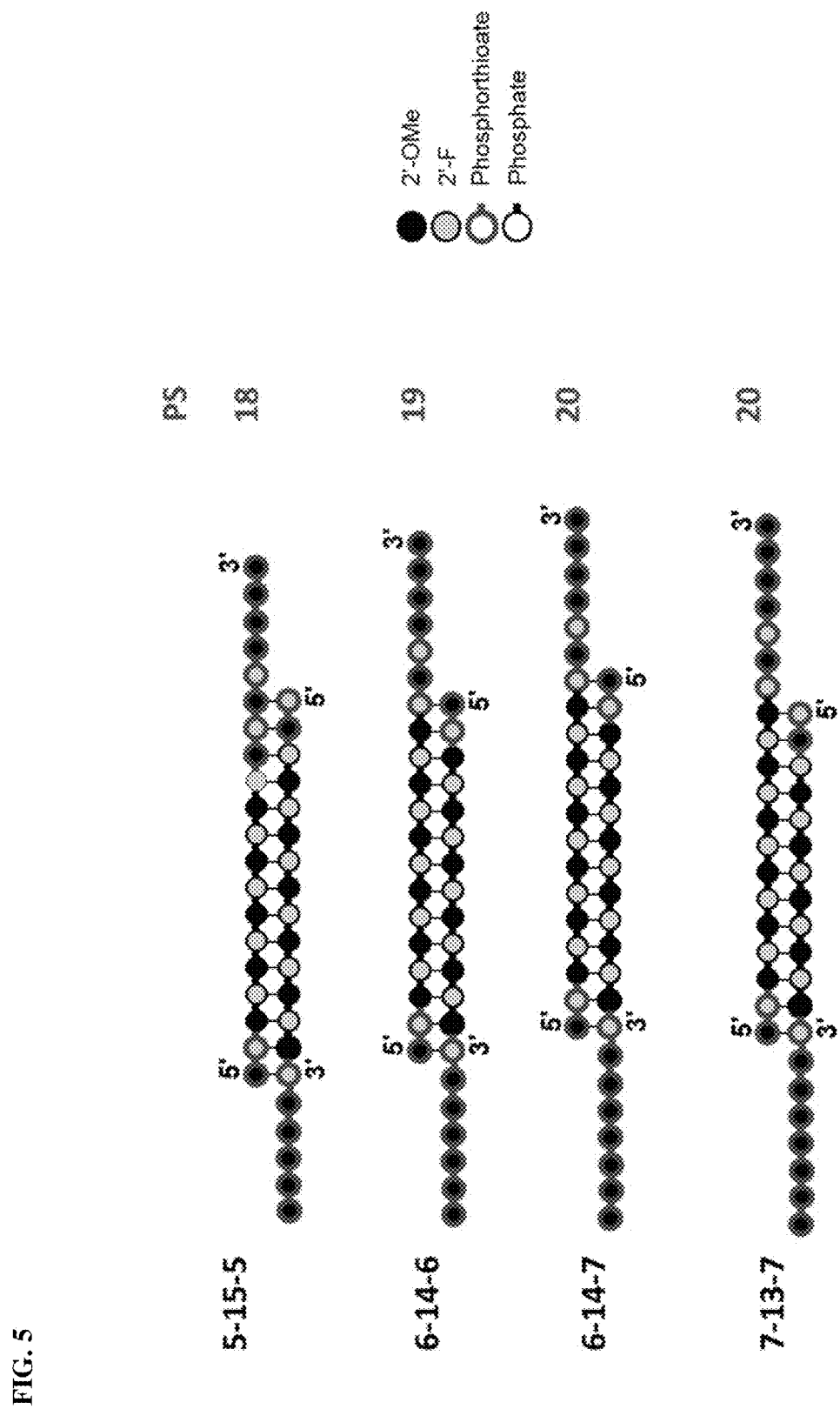
FIG. 5 depicts four examples of two-tailed siRNAs having phosphorothioated tails with differing lengths and increasing numbers of total phosphorothioates.

Two-tailed siRNAs (see FIGS. 2 and 5 for examples of tt-siRNA structures) were synthesized using modified (2'-F, 2'-OMe) phosphoramidates (Chemgenes, MA) under solid-phase synthesis conditions using a MerMade 12 (BioAutomation, Irving, Tex.), Expedite DNA/RNA synthesizer (ABI 8909) and an AKTA Oligopilot 10 and 100 (GE Healthcare Life Sciences, Pittsburgh, Pa.). Unconjugated oligonucleotide strands were grown on either controlled pore glass or Nittophase® functionalized with a long-chain alkyl amine terminated with Unylinker® (Chemgenes, #N-4000-10). Phosphorothioates were added using 0.1M 1,2,4-dithiazole-5-thione (DDTT) (Chemgenes, RN-1689) in place of standard iodine oxidation cycle. The oligonucleotides were deprotected using 40% methylamine (Aldrich, 426466) at 65° C. for 15 min. The oligonucleotides were lyophilized to dryness, re-suspended in water, and purified by anion exchange HPLC using sodium perchlorate (Fisher, S490-500) (0.1M) as the eluent on an Agilent PL-SAX HPLC column (Agilent, Santa Clara, Calif.) (Agilent PL-SAX, PL1751-3102, 1000 Å, 50×150 mm, 10 μm, or Agilent PL-SAX, PL1251-3102, 1000 Å, 25×150 mm, 10 μm).

HPLC was performed using either an Agilent 1100 or 1260 apparatuses. The salty oligonucleotides were then lyophilized to dryness, re-suspended in water and passed through a Sephadex (GE, G25, Fine in either a 50×250 mm or 25×250 column) size exclusion column to remove the salt. Finally, the oligonucleotides were lyophilized to dryness, quantitated, duplexed with their compliments and passed through a 0.22 μm filter. The oligonucleotides were checked by Liquid-Chromatography coupled Mass Spectrometry (LC-MS) using an Agilent 6530B Q-ToF apparatus to verify the purity and mass of each oligonucleotide. (Agilent AdvanceBio Oligonucleotide column, 2.1×150 mm, 2.7 μm using 1,1,1,3,3,3-Hexafluoro-2-propanol (0.1M)/Triethylamine (9 mM) (HFIP/TEA) as buffer and methanol as the eluent.) See sample tt-siRNAs targeting the huntingtin gene in Table 1.

Example 2

Two-tailed siRNA Efficacy in HeLa Cells

Figure 1:
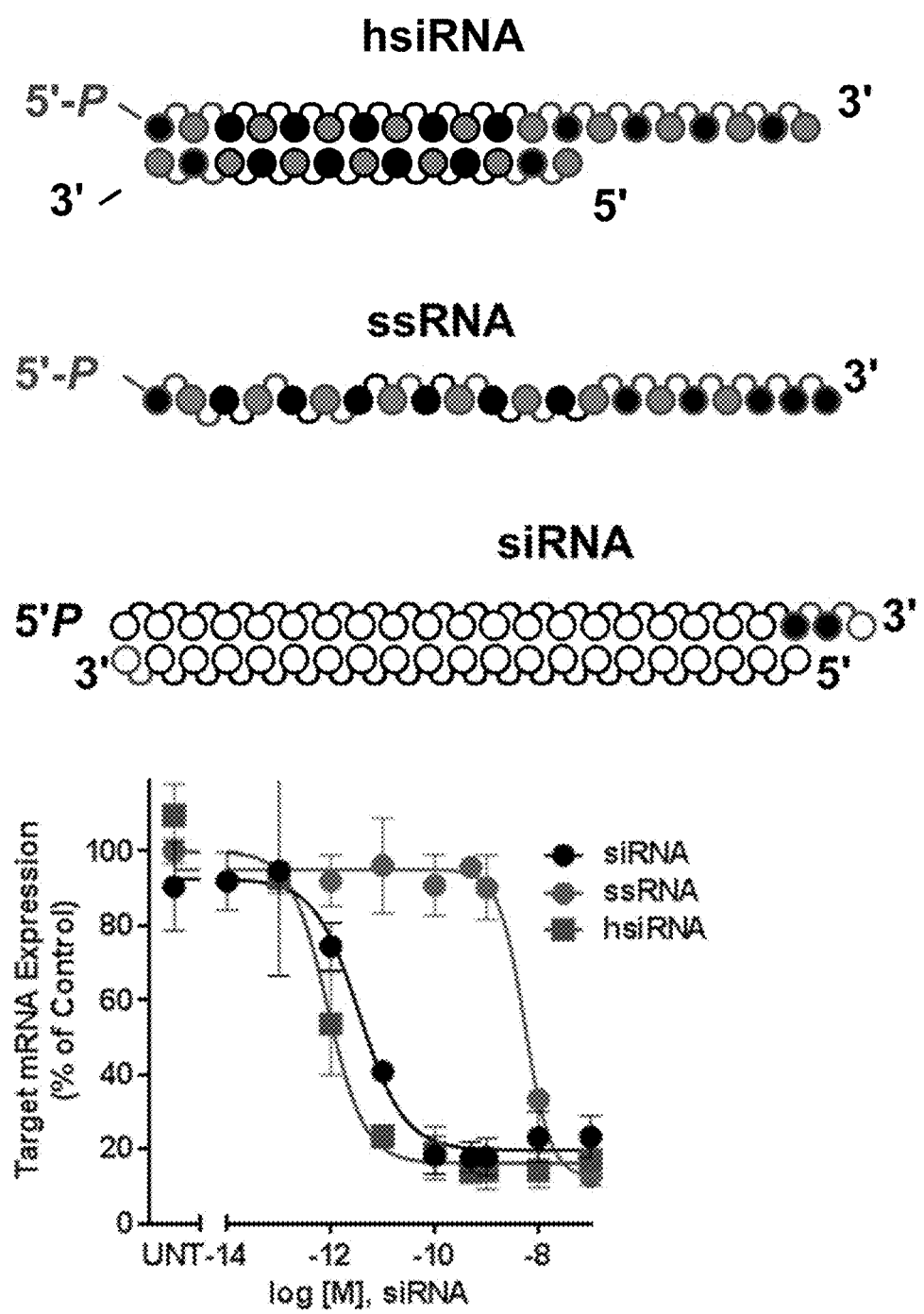
FIG. 1 depicts representative structures of siRNA, single stranded RNA (ssRNA), and one-tailed siRNA (hsiRNA) and a line graph that depicts mRNA expression in HeLa cells after treatment with siRNA, ssRNA, or hsiRNA.
Figure 3:
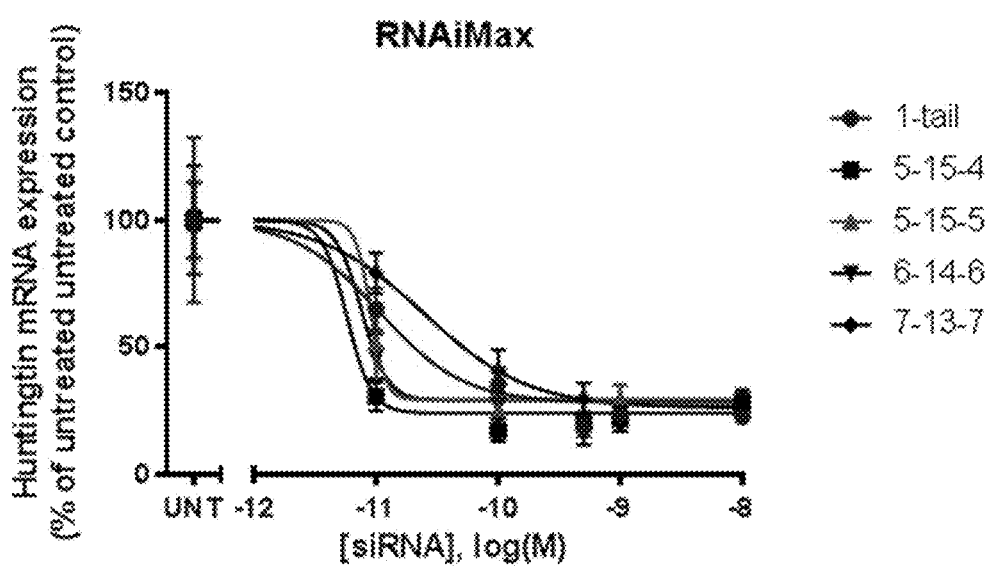
FIG. 3 depicts a line graph, which demonstrates that tt-siRNAs display efficient mRNA silencing in HeLa cells. Primary cortical mouse neurons were treated with two tailed siRNAs at concentrations shown for 1 week. mRNA was measured using Affymetrix QuantiGene 2.0. Data was normalized to housekeeping gene (PPIB) and graphed as % of untreated control.
Figure 4A:
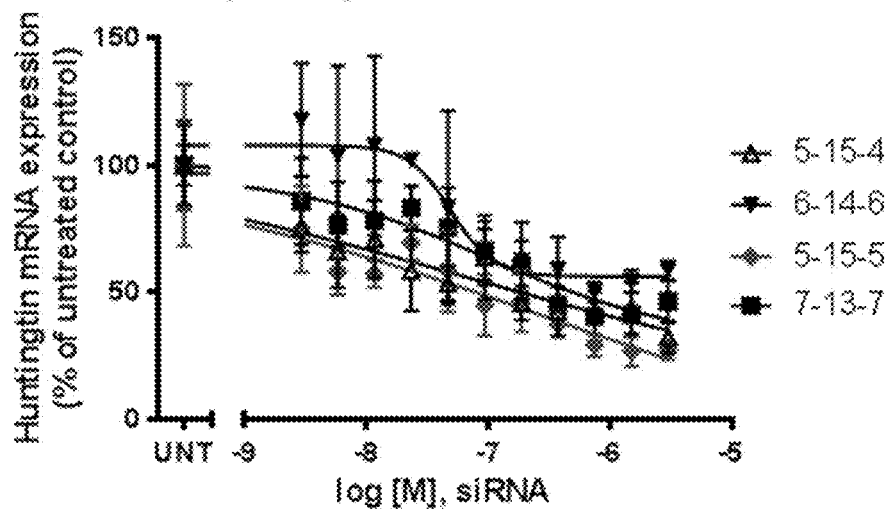
FIGS. 4A-B depict the efficiency of mRNA silencing by tt-siRNAs in primary cortical neurons.
Figure 4B:
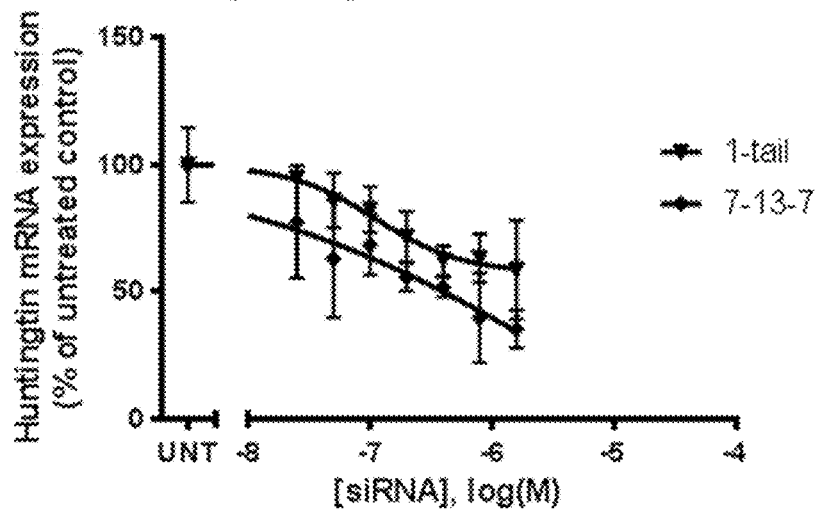

To compare the efficiency of RISC entry and silencing of two-tailed siRNAs (tt-siRNA) compared to one-tailed siRNAs (hsiRNA) and single strand RNAs (ssRNA), HeLa cells were transfected (using RNAiMax) with either tt-siRNA, hsiRNA, or ssRNA targeting Huntingtin mRNA at increasing concentrations (1 μm-10 nm) for 72 hours. Huntingtin mRNA silencing was then measured using Affymetrix QuantiGene 2.0. Data was normalized to housekeeping gene (PPIB) and graphed as % of untreated control. FIG. 1 shows that the addition of one phosphorothioated tail exhibited similar gene silencing efficacy as compared to an unmodified siRNA duplex. FIG. 3 shows that four different two-tailed siRNAs silenced Huntingtin mRNA at a similar efficacy to one-tailed siRNA, demonstrating that the two-tailed structure does not interfere with RISC loading and silencing. These results demonstrate that compounds of the invention efficiently enter RISC for further RNAi processing.

TABLE 1

Sample tt-siRNAs targeting the huntingtin gene. All sequences targeted the huntingtin gene (Accession number NM_002111.6) at position 10150. Chemical modifications are designated as follows: "." - phosphodiester bond; "#" - phosphorothioate bond; "m" - 2'-OMethyl; "f" - 2'-Fluoro; and "P" - 5' phosphate.

|  | Antisense strand | Sense strand |
|---|---|---|
| 7-13-7 | PmU#fU#mA.fA.mU.fC.mU.fC.mU.fU.mU.fA#mC#fU#mG#fA#mU#fA#mU#fA | fG#mU#fA.mA.fA.mG.fA.mG.fA.mU.fU.mA#fA#mU#mU#mU#mU#mU#mU#mU |
| 6-14-6 | PmU#fU#mA.fA.mU.fC.mU.fC.mU.fU.mU.fA#mC#fU#mG#fA#mU#fA#mU#fA | mA#fG#mU.fA.mA.fA.mG.fA.mG.fA.mU.fU.mA#fA#mU#mU#mU#mU#mU#mU |
| 5-15-5 | PmU#fU#mA.fA.mU.fC.mU.fC.mU.fU.mU.fA#mC#fU#mG#fA#mU#fA#mU#fA | fC#mA#fG.mU.fA.mA.fA.mG.fA.mG.fA.mU.fU.mA#fA#mU#mU#mU#mU#mU |
| 7-14-6 | PmU#fU#mA.fA.mU.fC.mU.fC.mU.fU.mU.fA#mC#fU#mG#fA#mU#fA#mU#fA | mA#fG#mU.fA.mA.fA.mG.fA.mG.fA.mU.fU.mA#fA#mU#mU#mU#mU#mU#mU |

Figure 10:
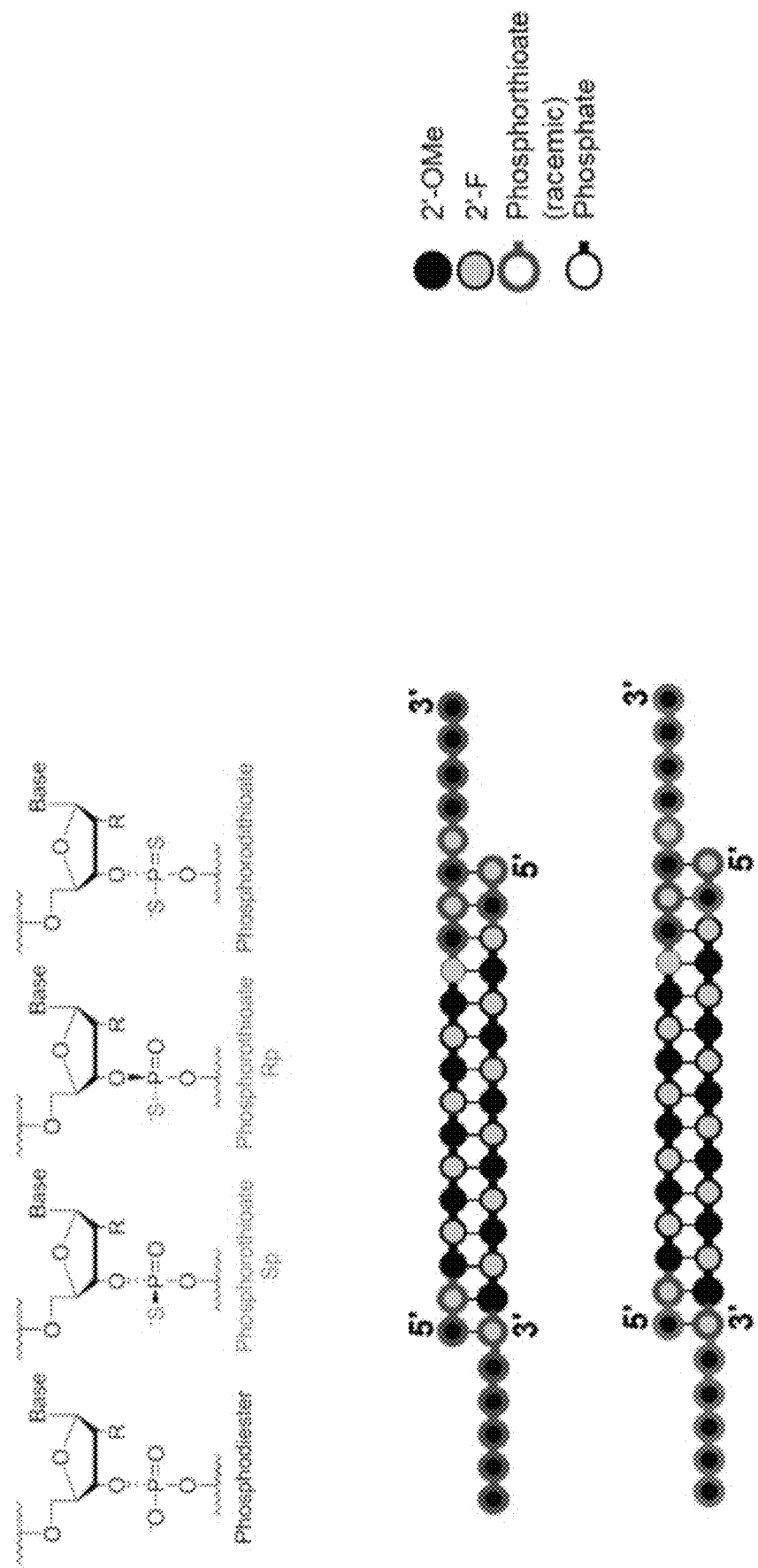
FIG. 10 depicts two-tailed siRNAs with stereoselective phosphorothioate content.

The phosphorothioate content in the tt-siRNAs of the invention can be made up of a racemic mixture of Rp and Sp stereoisomers, or can be synthesized with one or the other specifically to enhance stability and efficacy. Additionally, position specific changes in phosphorothioate stereoselectivity can be employed. Phosphorodithioate linkages can also be used at select positions to enhance hydrophobicity and protein association (see FIG. 10 for structures).

Abasic nucleotides, as well as phosphorothiates linked by carbon or tetraethylene glycol linkers, can also be used in place of single stranded phosphorothioate tails starting at position 18 on the guide strand, or at the 3' end of the passenger strand.

The oligonucleotide backbone can be made up of phosphates, phosphorothioates (a racemic mixture or stereospecific), diphosphorothioates, phosphoramidates, peptide nucleic acid, boranophosphate, 2'-5'phosphodiester, amide linked, phosphonoacetate, or morpholino, or a combination thereof (see FIG. 11 for structures).

Sugar modifications can include 2'O-methyl, 2'fluoro, 2'ribo, 2'deoxyribo, 2'F-ANA, MOE, 4'S-RNA, LNA, 4'S-F-ANA, 2'-O-Allyl, 2'-O-Ethylamine, CNEt-RNA, Tricyclo-DNA, CeNA, ANA, HNA, or a combination thereof (see FIG. 12 for structures).

As shown in FIG. 1, tt-siRNA showed equal efficacy relative to a one-tailed siRNA duplex following lipid-mediated transfection in HeLa cells, indicating that RISC loading was not hindered by the addition of a second single stranded tail. Two-tailed siRNA was not efficacious in HeLa cells without transfection, however in primary cortical neurons, tt-siRNAs promoted about 50% silencing, indicating that the addition of a phosphorothioated tail is an effective method for delivering siRNA to primary neurons, without formulation (e.g., without the addition of a hydrophobic moiety).

Figure 8:
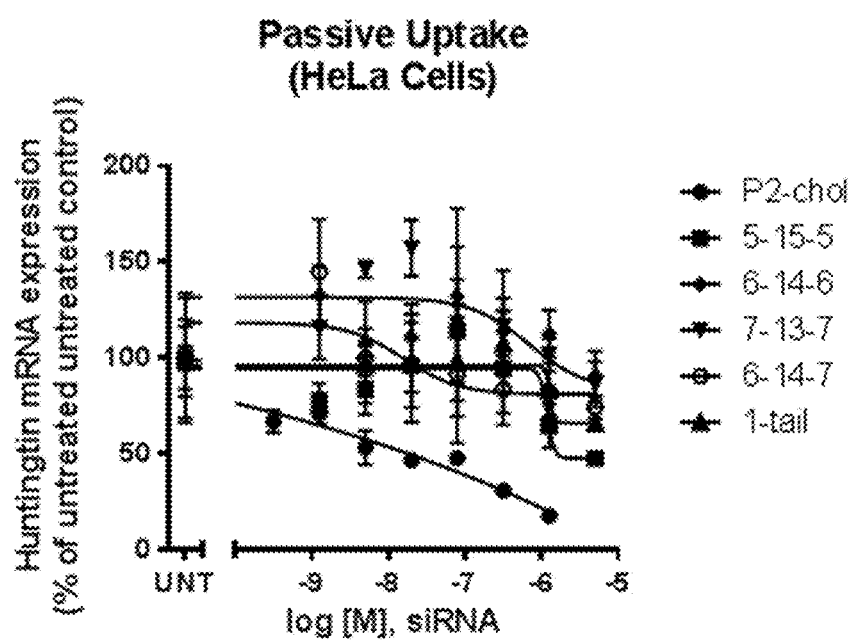
FIG. 8 depicts a line graph representing Huntingtin mRNA expression in HeLa cells after treatment with one-tailed siRNA or one of four different tt-siRNAs.
Figure 9A:
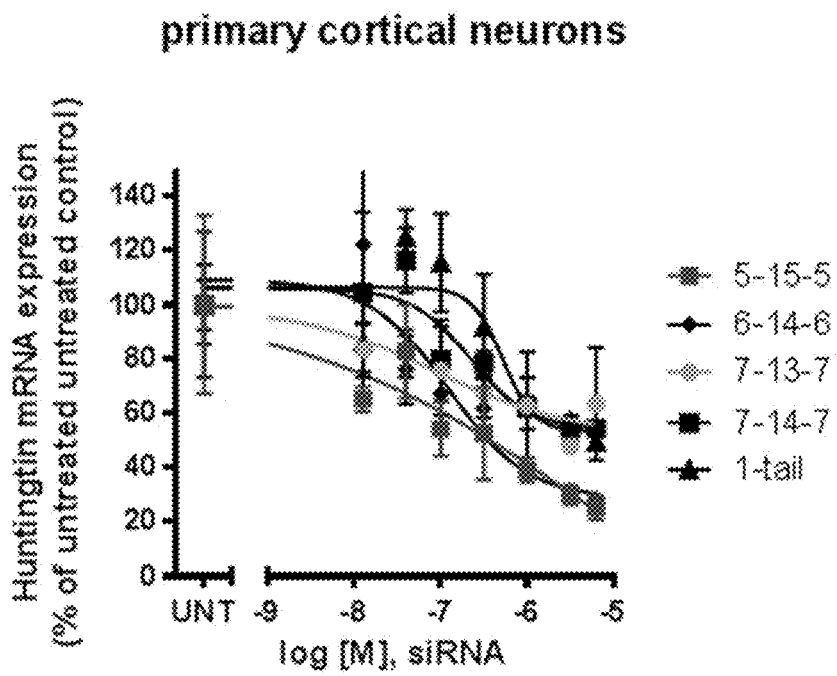
FIGS. 9A-B depict Huntingtin mRNA silencing in primary cortical neurons.
Figure 9B:
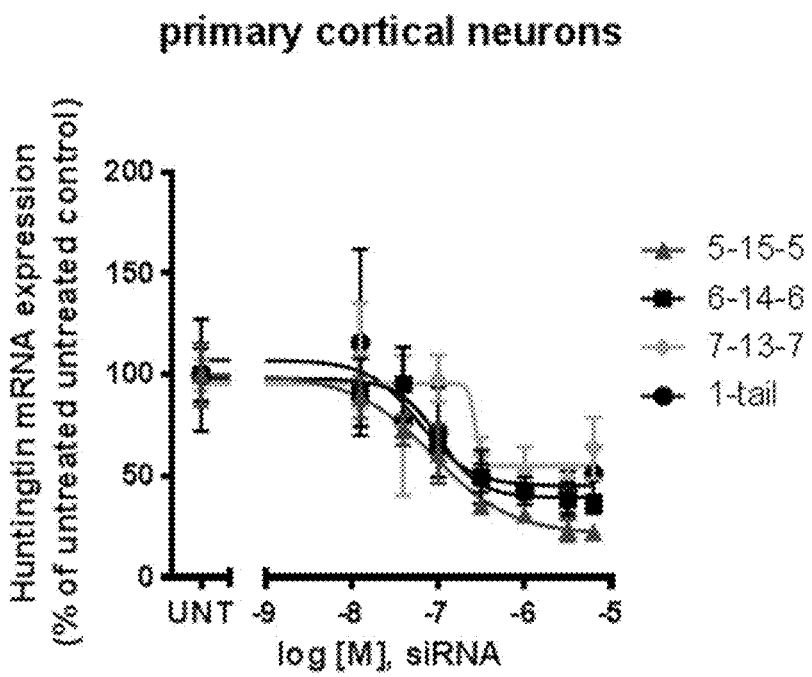

In order to determine the cellular uptake, HeLa cells were treated passively (i.e., with no transfection reagents) using two-tailed siRNAs targeting Huntingtin mRNA at increasing concentrations (1 nm-1 μm) for one week. The results of FIG. 8 show that there was no significant silencing of the Huntingtin mRNA with any of four different two-tailed siRNAs. However, in primary cortical neurons, passive uptake of tt-siRNA resulted in efficient gene silencing, see Example 3 below. This data indicated that the internalization and efficacy of two-single stranded phosphorothioated tails was cell-type specific. mRNA was measured using Affymetrix QuantiGene 2.0. Data was normalized to housekeeping gene (PPIB) and graphed as % of untreated control.

Example 3

Two-tailed siRNA Efficacy in Primary Cortical Neurons

Two-tailed phosphorothioation of siRNAs was determined to be efficient for delivery to primary neurons without the need for transfection reagents or hydrophobic modifications. The increased phosphorothioation of the additional single stranded tail supported increased efficacy as can be seen by comparing Huntingtin mRNA expression after treatment with the one-tailed siRNA to the two-tailed 7-13-7 siRNA (FIG. 3B).

Without intending to be bound by scientific theory, while the longer phosphorothioated single stranded tails in the 7-13-7 two-tailed siRNA provided superior distribution in vivo, the longer duplex region in the 5-15-5 two-tailed siRNA could be more conducive to efficacious silencing, as shown in the results of FIG. 3A.

Example 4

Two-tailed siRNA Internalization in Primary Cortical Neurons

Figure 6:
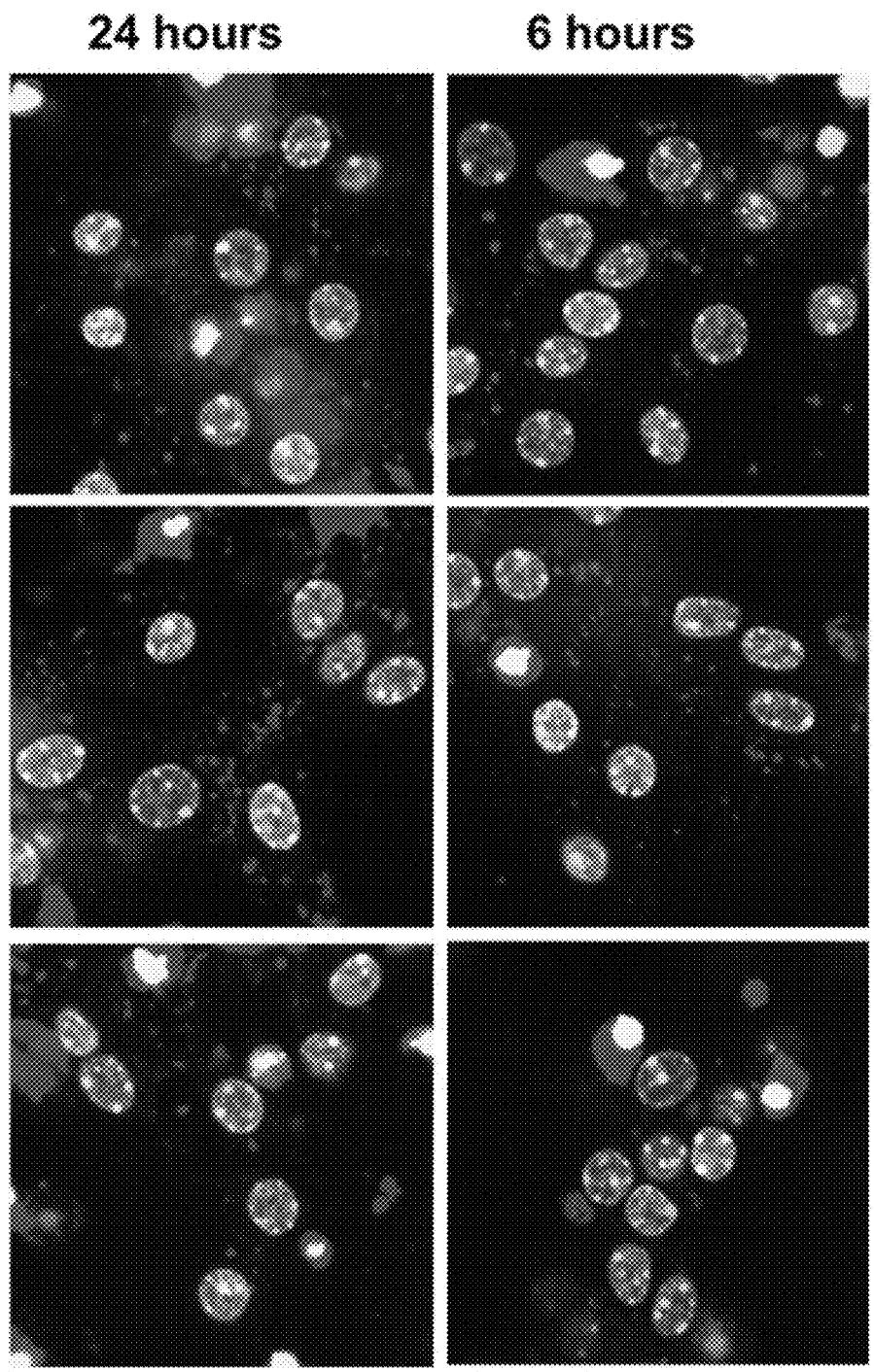
FIG. 6 depicts immunofluorescence images of primary neurons at 6 and 24 hours after treatment with tt-siRNAs (red=tt-siRNA, blue=DAPI).

Immunofluorescent analysis at the cellular level indicated that tt-siRNAs accumulated in primary cortical neurons at 6 hours and 24 hours post-injection (FIG. 6). These results demonstrate the ability of the tt-siRNAs to efficiently enter neurons. Artificial cerebrospinal fluid (aCSF) was used as a negative control.

In some embodiments, compounds of the invention promote about 50% silencing in primary cortical neurons upon treatment of the neurons with no transfection formulation (i.e., by passive uptake). In some embodiments, compounds of the invention exhibit about 70% silencing in HeLa cells upon treatment of the cells with a transfection reagent.

Treatment of primary cortical neurons with tt-siRNAs induces robust mRNA silencing. This level of efficacy has never been demonstrated previously for one-tailed siRNAs.

Example 5

Route of Administration of Two-Tailed siRNAs In Vivo

Figure 7:
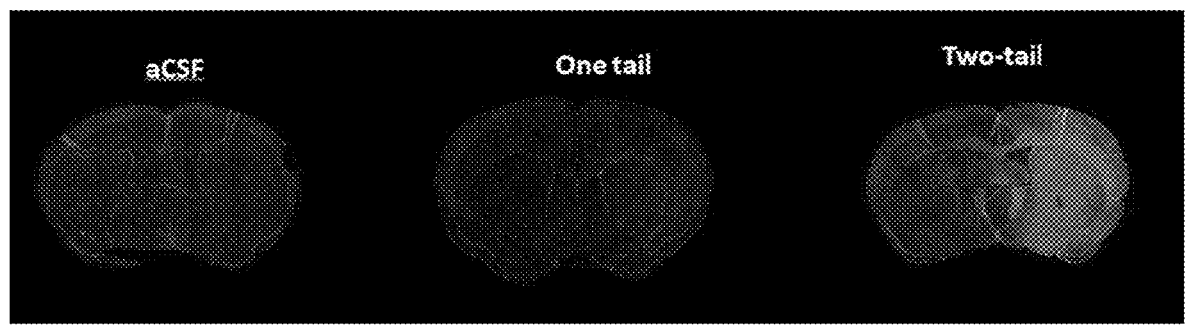
FIG. 7 depicts immunofluorescence images of 300 µm brain sections 48 hours after intrastriatal injections of a negative control, one-tailed siRNAs, or tt-siRNAs (red=tt-siRNA, blue=DAPI).

To assess the efficacy of delivery of two-tailed siRNAs in vivo in neurons, tt-siRNA was delivered to mice via intrastriatal (IS) injection. tt-siRNA localized to and accumulated throughout the injected hemisphere of the brain, whereas the one-tailed siRNA showed significantly lower accumulation in the injected hemisphere of the brain (FIG. 7).

As shown in FIG. 7, tt-siRNAs distributed throughout the injected hemisphere of the mouse brain following intrastriatal injection. While one-tailed siRNA could silence mRNA in primary neurons, the tt-siRNA structure was critical for enhanced tissue distribution and tissue retention of siRNAs. The subtle hydrophobicity of the two single-stranded phosphorothioated tails supported tissue retention while also allowing for widespread and uniform distribution throughout the ipsilateral hemisphere of the injected brain.

As shown in FIG. 7, a single injection of tt-siRNA was detected both ipsilateral and contralateral to the injection site, indicating that spread is not limited to the injected hemisphere, but is also occurring across the midline into the non-injected side. Without intending to be bound by scientific theory, alternative methods of injection, including intracerebral ventricular, could also facilitate bilateral distribution with only one injection.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by exemplary embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

What is claimed is:

1. A double-stranded nucleic acid compound comprising:
   a) a sense strand having a 5' end, a 3' end and a region of complementarity with an antisense strand;
   b) an antisense strand having a 5' end, a 3' end, a region of complementarity with target RNA;
   c) a first overhang region at the 3' end of the sense strand having at least 4 contiguous phosphorothioated nucleotides; and
   d) a second overhang region at the 3' end of the antisense strand having at least 4 contiguous phosphorothioated nucleotides,
   wherein the nucleotides at positions 1 and 2 from the 5' end of the sense and antisense strands are connected to adjacent nucleotides via phosphorothioate linkages.

2. The compound of claim 1, wherein the antisense strand comprises a 5' phosphate moiety.

3. The compound of claim 1, wherein the antisense strand comprises a moiety R at the 5' end, wherein R is selected from the group consisting of:

R1 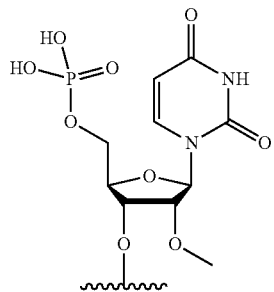

R2 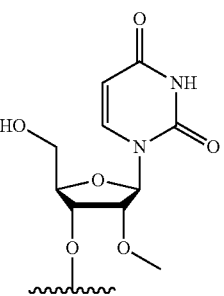

R3 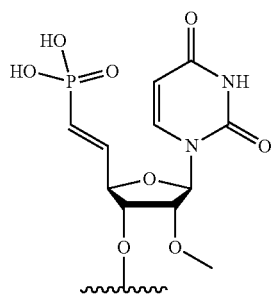

R4 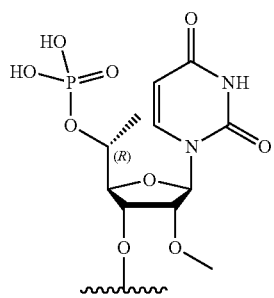

R5 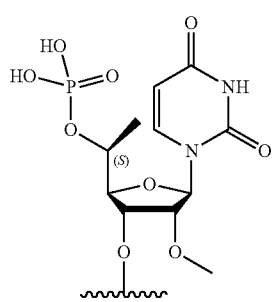

R6 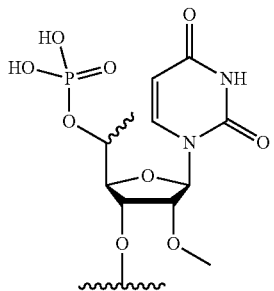

R7 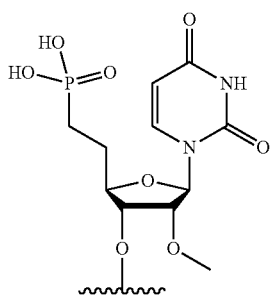

R8 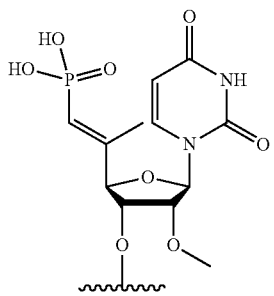

4. The compound of claim 1, wherein the sense strand and the anti sense strand each independently comprise at least 15 contiguous nucleotides.

5. The compound of claim 1, wherein the overhang regions of the sense strand and the antisense strand independently comprise 2'-methoxy-nucleotides and 2'-fluoro-nucleotides.

6. The compound of claim 5, wherein the overhang region of the sense strand and the antisense strand independently consists of at least four consecutive 2'-methoxy-nucleotides.

7. The compound of claim 6, wherein the nucleotides at positions 1, 2, 3, and 4 from the 3' end of the sense and antisense strands consist of 2'-methoxy-nucleotides.

8. The compound of claim 1, wherein the nucleotides at positions 1-7 or 1-8 from the 3' end of the sense strand or the 3' end of the antisense strand, independently, are connected to adjacent nucleotides via phosphorothioate linkages.

9. The compound of claim 1, wherein the overhang regions of the sense strand and the antisense strand have the same number of phosphorothioated nucleotides.

10. The compound of claim 3, having the structure selected from Formulas (I-VIII):

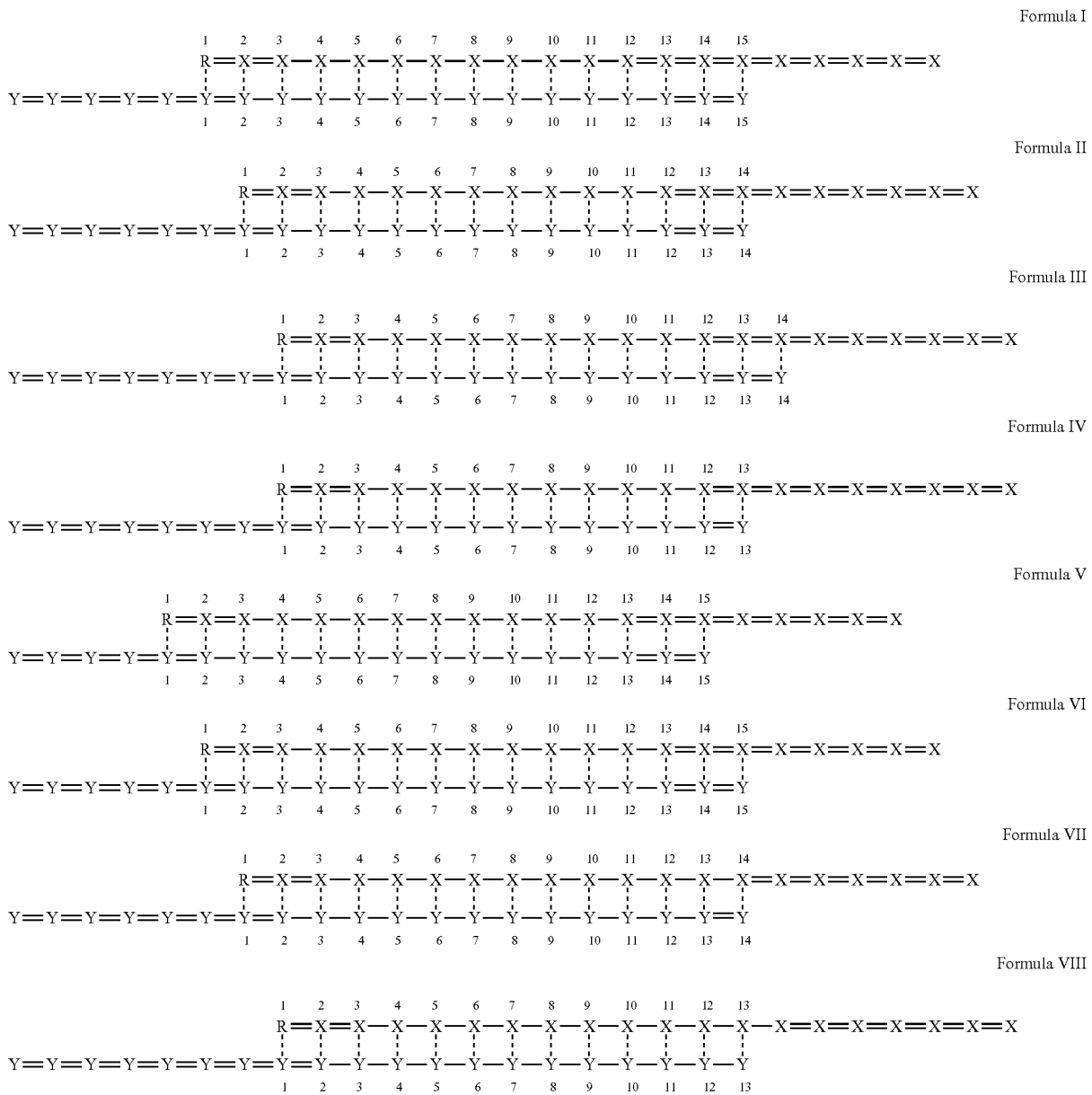

wherein:
X, for each occurrence, independently, is selected from adenosine, guanosine, uridine, cytidine, and chemically-modified derivatives thereof;
Y, for each occurrence, independently, is selected from adenosine, guanosine, uridine, cytidine, and chemically-modified derivatives thereof;
- represents a phosphodiester internucleoside linkage;
= represents a phosphorothioate internucleoside linkage;
--- represents, individually for each occurrence, a base-pairing interaction or a mismatch; and
R, for each occurrence, is a nucleotide comprising a 5' phosphate or is R1, R2, R3, R4, R5, R6, R7 or R8, as defined above.

11. The compound of claim 1, wherein the antisense strand has between 80% and 99% complementarity to the target RNA.

12. A pharmaceutical composition comprising one or more double stranded nucleic acid compounds of claim 1, and a pharmaceutically acceptable carrier.

13. A method of treating a disease or disorder comprising administering to a subject in need of such treatment a therapeutically effective amount of the pharmaceutical composition of claim 12.

14. The method of claim 13, wherein the subject in need of such treatment is a human.

15. A method for selective in vivo delivery of a compound of claim 1 to a target organ, tissue or cells, comprising administering the compound to a subject.

16. A method of treating a neurological disease or disorder comprising administering to a subject in need of such treatment a therapeutically effective amount of the pharmaceutical composition of claim 12.

17. A method of treating a neurological disease or disorder comprising administering to a subject in need of such treatment a therapeutically effective amount of the double stranded nucleic acid compound having the structure of Formula (I) or Formula (VI), or Formula (IV) or Formula (VII) of claim 10.

18. The method of claim 17, wherein the pharmaceutical composition is administered by intravenous injection, intraperitoneal injection, intracranial injection, intrathecal injection, intrastriatal injection, or intracerebroventricular injection.

19. A double-stranded nucleic acid compound comprising
   a) a sense strand having a 5' end, a 3' end and a region of complementarity with an antisense strand;
   b) an antisense strand having a 5' end, a 3' end, a region of complementarity with target RNA;
   c) a first overhang region at the 3' end of the sense strand having 7 contiguous phosphorothioated nucleotides; and
   d) a second overhang region at the 3' end of the antisense strand having 7 contiguous phosphorothioated nucleotides.

20. A double-stranded nucleic acid compound comprising:
   a) a sense strand having a 5' end, a 3' end and a region of complementarity with an antisense strand;
   b) an antisense strand having a 5' end, a 3' end, a region of complementarity with target RNA;
   c) a first overhang region at the 3' end of the sense strand comprising at least 4 contiguous phosphorothioated nucleotides; and
   d) a second overhang region at the 3' end of the antisense strand comprising at least 5 contiguous phosphorothioated nucleotides.

21. The compound of claim 5, wherein the overhang regions of the sense strand and the antisense strand consist of 2'-methoxy-nucleotides.

22. The compound of claim 1, wherein the overhang region of the sense strand and the antisense strand independently consists of 4, 5, 6, 7, or 8 phosphorothioated nucleotides.

23. The compound of claim 1, wherein the overhang regions of the sense strand and the antisense strand have different numbers of phosphorothioated nucleotides.

24. The compound of claim 1, wherein the overhang comprises abasic nucleotides.

25. The compound of claim 1, wherein the antisense strand has perfect complementarity to the target RNA.

26. The method of claim 16, wherein the neurological disease or disorder is Huntington's disease.

27. The method of claim 15, wherein the target organ is the brain.

28. The method of claim 15, wherein the target cells are primary cortical neurons.

29. The method of claim 15, wherein the delivery of the compound is not mediated by lipid formulation.

30. The method of claim 15, wherein the compound is administered by intravenous injection, intraperitoneal injection, intracranial injection, intrathecal injection, intrastriatal injection, or intracerebroventricular injection.

* * * * *